(12) United States Patent
Roth et al.

(10) Patent No.: US 9,903,859 B2
(45) Date of Patent: Feb. 27, 2018

(54) METHOD FOR IDENTIFYING APTAMERS

(71) Applicants: HELMHOLTZ-ZENTRUM FUER UMWELTFORSCHUNG GMBH—UFZ, Leipzig (DE); ALBERT-LUDWIGS-UNIVERSITAET FREIBURG, Freiburg im Breisgau (DE)

(72) Inventors: Guenter Roth, Freiburg im Breisgau (DE); Christine Reinemann, Leipzig (DE); Beate Strehlitz, Leipzig (DE)

(73) Assignee: Albert-Ludwigs-Universitaet Freiburg, Freiburg im Breisgau (DE)

(*) Notice: Subject to any disclaimer, the term of this patent is extended or adjusted under 35 U.S.C. 154(b) by 86 days.

(21) Appl. No.: 14/354,597

(22) PCT Filed: Oct. 25, 2012

(86) PCT No.: PCT/EP2012/071155
§ 371 (c)(1),
(2) Date: Apr. 28, 2014

(87) PCT Pub. No.: WO2013/060777
PCT Pub. Date: May 2, 2013

(65) Prior Publication Data
US 2014/0303030 A1    Oct. 9, 2014

(30) Foreign Application Priority Data
Oct. 28, 2011 (DE) .................. 10 2011 085 473

(51) Int. Cl.
| | | |
|---|---|---|
| C12Q 1/68 | (2006.01) |
| C07H 21/02 | (2006.01) |
| C07H 21/04 | (2006.01) |
| G01N 33/53 | (2006.01) |
| C12N 15/10 | (2006.01) |
| C12N 5/00 | (2006.01) |

(52) U.S. Cl.
CPC ..... *G01N 33/5308* (2013.01); *C12N 15/1048* (2013.01); *C12Q 1/6811* (2013.01)

(58) Field of Classification Search
None
See application file for complete search history.

(56) References Cited

U.S. PATENT DOCUMENTS

| | | | |
|---|---|---|---|
| 6,143,496 A | 11/2000 | Brown et al. | |
| 6,300,007 B1 | 10/2001 | Boles et al. | |
| 6,300,070 B1 | 10/2001 | Boles et al. | |
| 7,244,559 B2 | 7/2007 | Rothberg et al. | |
| 7,323,305 B2 | 1/2008 | Leamon et al. | |
| 7,335,762 B2 | 2/2008 | Rothberg et al. | |
| 7,638,276 B2 | 12/2009 | Griffiths et al. | |
| 8,680,017 B2 * | 3/2014 | Lopreato ............ | C12N 15/1048 506/9 |
| 2009/0075834 A1 * | 3/2009 | Doyle .................. | C12N 15/115 506/9 |
| 2009/0127589 A1 | 5/2009 | Rothberg et al. | |
| 2010/0055677 A1 | 3/2010 | Colston, Jr. et al. | |
| 2010/0297671 A1 | 11/2010 | Tschmelak et al. | |
| 2011/0105364 A1 | 5/2011 | Kurn | |
| 2011/0245101 A1 | 10/2011 | Chee et al. | |
| 2011/0251088 A1 * | 10/2011 | Lopreato ............ | C12N 15/1048 506/9 |
| 2011/0262922 A1 | 10/2011 | Chae et al. | |
| 2013/0274113 A1 * | 10/2013 | Kim ...................... | C12N 15/111 506/1 |

FOREIGN PATENT DOCUMENTS

| | | |
|---|---|---|
| WO | 2008/022332 A2 | 2/2008 |
| WO | 2009/151688 A2 | 12/2009 |
| WO | WO2009151688 A2 * | 12/2009 |
| WO | 2010/100265 A1 | 9/2010 |
| WO | WO2010100265 * | 9/2010 |
| WO | WO2010100265 A1 * | 9/2010 |

OTHER PUBLICATIONS

Miller et al. (Journal of immunological methods 365.1 (2011): 118-125.).*
Lou et al.( Proceedings of the National Academy of Sciences 106.9 (2009): 2989-2994).*
M. Cho et al: "Quantitative selection of DNA aptamers through microfluidic selection and high-throughput sequencing", in: Proceedings of the National Academy of Sciences, vol. 107, No. 35, Aug. 31, 2010, pp. 15373-15378.
Peng Lu et al: "A combined atomic force/fluorescence microscopy technique to select aptamers in a single cycle from a small pool of random oligonucleotides.", in: Microscopy Research and Technique Apr. 2007, vol. 70, No. 4, Apr. 2007, pp. 372-381.
Mark Platt et al: "Analysis of aptamer sequence activity relationships", Integrative Biology, vol. 1, No. 1, Jan. 1, 2009, p. 116.
Keke Shao et al: "Emulsion PCR: A High Efficient Way of PCR Amplification of Random DNA Libraries in Aptamer Selection", in: PLOS ONE, vol. 6, No. 9, Jan. 1, 2011, p. e24910.

(Continued)

*Primary Examiner* — Sean McGarry
(74) *Attorney, Agent, or Firm* — Agris & Von Natzmer, LLP; Joyce Von Natzmer

(57) ABSTRACT

The invention relates to a method for identifying aptamers, having the following steps —bringing a mixture of oligonucleotides into contact with an aptamer target structure and binding at least some of the oligonucleotides to the target structure, —separating the oligonucleotides which have been bound to the aptamer target structure from the aptamer target structure and from oligonucleotides that are not bound to the aptamer target structure, —amplifying individual oligonucleotides which were bound to the aptamer target structure in a physically separate manner and producing a plurality of physically separate amplicons, each amplicon predominantly containing one type of oligonucleotides, —specifying a specific marker for a plurality of the physically separate amplicons such that each of the marked amplicons can be uniquely identified using the specified marker of the amplicon, —sequencing oligonucleotides in a plurality of marked amplicons and assigning the marker that is specific for the amplicon to the sequence of the type of oligonucleotides in the amplicon for each amplicon examined by means of the sequencing process —analyzing the binding properties of the types of oligonucleotides to the aptamer target structure and assigning the analyzed binding properties to the specific markers of the amplicons and to the sequences of the types of oligonucleotides.

19 Claims, 5 Drawing Sheets

(56) References Cited

OTHER PUBLICATIONS

JPN6016029959, "How is genome sequencing done ?", [online]. Jul. 7, 2011.
Sandberg et al., Rapid flow-sorting to simultaneously resolve multiplex massively parallel sequencing products, Oct. 6, 2011; Scientific Reports, 1:108, DOL:10.1038/srep00108.
Shao et al., Emulsion PCR: A High Efficient Way of PCR Amplification of Random DNA Libraries in Aptamer Selection, PLoS ONE Sep. 15, 2011; vol. 6, Issue 9, e24910.
Jolma et al., Multiplexed massively parallel SELEX for characterization of human transcription factor binding specificities, 2010; 20:861-873, ISSN 1088-9051/10.
Berezovski et al., Non-SELEX: selection of aptamers without intermediate amplification of candidate oligonudeotides, Oct. 26, 2006; Nature Protocols, vol. 1 No. 3, 1359-1369.

\* cited by examiner

METHOD FOR IDENTIFYING APTAMERS

This is the U.S. national stage of International application PCT/EP2012/071155, filed Oct. 25, 2012 designating the United States and claiming priority to German application DE 10 2011 085 473.8, filed Oct. 28, 2011.

The present invention relates to a method for the identification of aptamers, an array of aptamers and a device for the identification of aptamers.

Aptamers are synthetic oligonucleotides that have been selected from an oligonucleotide library for their binding properties with respect to a desired target structure, also referred to as the target. The development of DNA aptamers has so far taken place according to an in vitro selection procedure, in which the molecules with the best binding properties for the target are selected from a complex library of approx. $10^{15}$ different molecules. This method is known as SELEX (systematic evolution of ligands by exponential enrichment) and the principles for this method were described in 1990 (Ellington, A. D., Szostak, J. W., Nature 346 (1990), 818-822; Tuerk, C., Gold, L., Science 249 (1990), 505-510; Robertson, D. L., Joyce, G. F., Nature 344 (1990), 467-468). The SELEX process is used in many variations for aptamer selection (Stoltenburg, R., Reinemann, C., Strehlitz, B., Biomol. Eng. 24 (2007), 381-403).

The SELEX process for producing DNA aptamers is an iterative process. It starts with a chemically synthesized DNA library of approx. $10^{15}$ different sequences. The individual DNA molecules of the library have a randomized sequence with a sequence region 20 to 80 nucleotides long, for example, flanked by specific primer sequences on the 3' and 5' ends with a length of 18 to 21 nucleotides, which are the same in each element of the library. A process cycle, which is also referred to as a (selection) round, consists of the steps:
- binding to the target,
- removal of unbound DNA,
- elution of the bound DNA from the target,
- amplification of the previously bound DNA by means of PCR,
- and extraction of the relevant ssDNA from the PCR products.

The result of the previous round is the starting material for the next round in each case. After approx. 6 to 20 rounds, sequence patterns that have a high affinity and specificity for the target should be enriched. The driving force of this evolutionary process is the selection conditions, which are determined by the properties of the target, for example, its concentration, the buffer conditions of the solution, the temperature, the incubation time, the efficiency of the separation of unbound DNA, introduction of negative selection steps, etc. The affinity and specificity of the aptamers depend on the stringency of the conditions, which can be adapted in the course of the selection rounds. The functionality of the aptamers, i.e., their ability to bind to the target, is established by the three-dimensional structure, which depends on their primary sequence, the length of the nucleic acid molecules preferably <100 nucleotides and the ambient conditions. Aptamers form typical structural patterns, such as stems, internal loops, tetra loops, triplicates, pseudoknots, hairpin structures, kissing complexes or G-quadruplex structures. Aptamers enter into adaptive conformational changes in the presence of the target, so that their three-dimensional folding forms a specific binding site for the target (induced fit). The binding between aptamer and target is based on various intermolecular interactions such as structural compatibility, stacking of aromatic rings with the nucleic acid basis of the aptamers, electrostatic interactions between charged groups and hydrogen bridge bonds.

Aptamers have been developed for a wide variety of targets: inorganic and small molecules, peptides, proteins, carbohydrates, antibiotics. Complex targets, such as whole cells and organisms as well as target mixtures have been used for aptamer selections. Toxic and non-immunogenic targets, for example, which are not accessible for antibody production, may also be used. After their selection and sequence analysis, the aptamers are produced by means of chemical synthesis, where reproducibility is ensured and the amount is in principle unlimited. Modifications of the aptamers are simple to perform, for example, for immobilization on sensor surfaces or chip surfaces, for quantification or for improvement of stability. The aptamer binding is reversible and denatured aptamers can be regenerated.

Both are major advantages for analytical use of aptamers. Aptamers have a great similarity with antibodies with respect to the binding behavior. Many of their properties make aptamers serious or even superior alternatives to antibodies. This is due mainly to the reversible denaturing, the much better stability in storage and the higher chemical stability.

In addition to the SELEX process, two other processes are known for aptamer selection. The Monolex process by the Aptares company also begins with an oligonucleotide library. After affinity adsorption of the oligonucleotide library, an affinity sorting of the oligonucleotides is performed on an adsorption bed and oligonucleotides of different affinities are separated into different pools. These pools are each amplified, which then yields polyclonal aptamer pools, each having a certain affinity. To obtain the individual (monoclonal) aptamers, the respective pool of polyclonal aptamers is cloned and sequenced.

One process for producing Spiegelmers is used by the company NOXXON for development of RNA aptamers as pharmaceuticals. Using this process, RNA ligands, so-called Spiegelmers, which contain L-ribose as the sugar component instead of D-ribose, have been developed. The incorporation of L-ribose into the sugar-phosphate backbone of the nucleic acid causes the three-dimensional structure of an L-RNA to behave like the mirror image of the structure of the corresponding D-RNA. L-RNA molecules are protected from enzymatic cleavage by nucleases and are therefore much more stable than the corresponding D-RNA. Ligands to the enantiomer of the actual target structure are selected first by using in vitro evolution. Once these ligands have been found, cloned, sequenced and characterized, the corresponding L-ribonucleic acid, the Spiegelmer, is synthesized chemically. Then by testing the binding properties of the ligand with respect to its actual target molecule and also with respect to its enantiomer, conclusions can be drawn about the affinity and specificity of the Spiegelmer.

As mentioned above, sequence patterns with a high affinity and specificity for the target should have become enriched in a SELEX process after approx. 6 to 20 rounds. Next, the binding oligonucleotides are cloned from the enriched oligonucleotide pool for isolation and are transformed in *E. coli*, for example. This is followed by additional steps such as verification of the positive transformants with regard to the correctness of the plasmid DNA (pDNA) and the incorporated insert (PCR product) and the preparation of the pDNA.

Disadvantages of this processing include the fact that it is relatively time-consuming to run through up to 20 SELEX rounds plus the extensive work following the SELEX process. If the selection conditions are not selected advantageously during one of the up to 20 SELEX rounds, good binders may be lost. After cloning in the previous process, the selection of aptamers to be marked further is made randomly, so that individual good binders may again be lost because they are not selected randomly, are not marked further and therefore are not detected as aptamers.

BRIEF DESCRIPTION OF THE DRAWINGS

FIG. 1).

FIG. 2A shows the particles 10 and oligonucleotides 7b-7e placed into the cavities 15 of a sequencer chip 14. In FIG. 2B, a support 18 (second support) is applied and complementary strands 7b', 7c', 7d', 7e' of the oligonucleotides 7b, 7c, 7d, 7e are produced. FIG. 2C shows the results of deposition of the copies 7b', 7c', 7d', 7e' on the binding adapters 22. In FIG. 2D support 18 with the negative copies 7b', 7c', 7d', 7e' bound to it is removed from the sequencer chip 14.

SUMMARY OF THE INVENTION AND DESCRIPTION OF VARIOUS AND PREFERRED EMBODIMENTS

Figure 1:
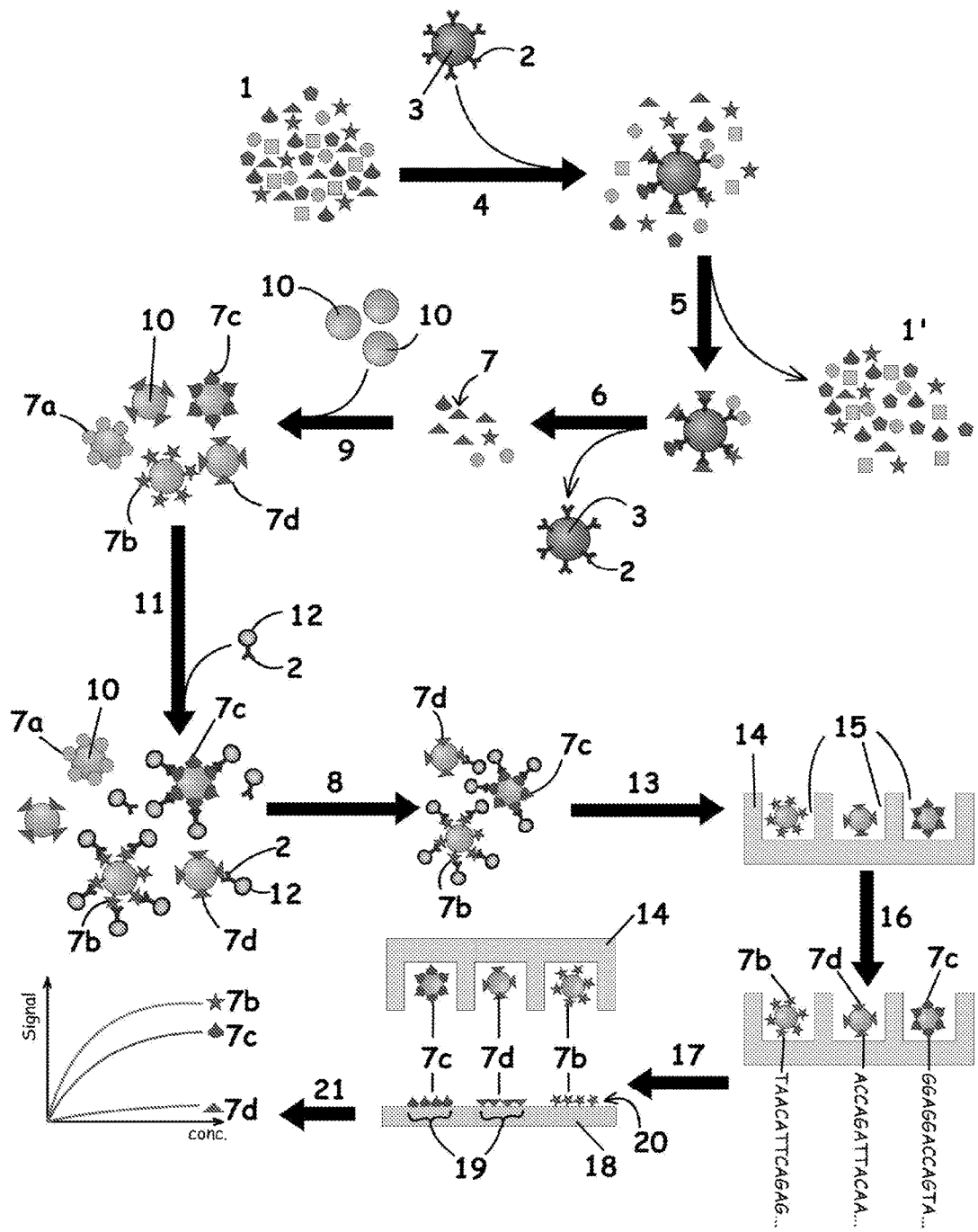
FIG. 1 provides an overview of initiating the disclosed method including placing particles 10 in each of the cavities 15, each of these particles having millions of copies of one oligonucleotide each 7b, 7c, 7d (cf.

One object of the present invention was to provide a method that would not have these disadvantages.

This object is achieved by a method for identification and/or production of aptamers, comprising bringing a mixture of oligonucleotides in contact with an aptamer-target structure and binding at least some of the oligonucleotides to the target structure, separating the oligonucleotides that are bound to the aptamer-target structure from the aptamer-target structure and from oligonucleotides not bound to the aptamer-target structure, spatially separate amplification of individual oligonucleotides that are bound to the aptamer-target structure and creating several spatially separate amplicons, wherein each amplicon primarily contains a type of oligonucleotide with an identical sequence, issuing a specific identification to a plurality of the spatially separate amplicons, preferably to all the spatially separate amplicons, so that each amplicon that has been marked is unambiguously identifiable on the basis of its specific marker, sequencing oligonucleotides in a plurality of marked amplicons, preferably in all marked amplicons, and assigning the specific marker for the amplicon to the sequence of the type of oligonucleotide in the amplicon, preferably for each amplicon investigated with sequencing, analyzing the binding properties of types of oligonucleotides to the aptamer-target structure and assigning the analyzed binding properties to the specific markers of the amplicons and the sequences of the types of oligonucleotides.

This process for aptamer identification/production proceeds much more rapidly than the SELEX process. It is no longer necessary to perform multiple rounds of the process but instead is sufficient to perform a simple selection.

This eliminates the extensive work that follows the SELEX process, the cloning to isolate the binding oligonucleotides from the enriched pool. After cloning, the aptamers to be characterized further are selected randomly in the traditional process, so that individual good binders may be "lost" because they are not randomly selected, not characterized further and therefore are not detected as aptamers. However, in the new process described here, all the bound oligonucleotides are isolated, sequenced and analyzed in a highly parallel procedure. The aptamers are selected as binders with the highest affinities at the end of the process, based on the measured affinities. This novel method thus achieves an increased yield, based on its design, and allows a better evaluation of the aptamers thereby obtained.

Using this process, it is possible to identify aptamers within a shorter period of time and at the same time to determine their sequence and binding constants for the target within the process. This process offers all the advantages of the SELEX process but now there is the possibility of terminating the process and identifying binding aptamers after a first selection step (binding, removal of the non-binders, elution of the binders from the target), which can be performed according to the steps of the known SELEX process. Due to the optional use of an additional binding and selection step to be evaluated even during the preparation for the sequencing, there is also a possibility of achieving a much higher specificity than in the SELEX process.

Additional advantages that can be achieved with the present invention and/or with special embodiments that are described below include:

The possibility of parallel sequencing and analysis of the binding properties of a very large number of potential aptamers. The sequencing by means of variants described below allows parallel sequence analysis of up to $10^6$ oligonucleotides. Thus, up to $10^6$ oligonucleotides can be selected, analyzed and validated in a single pass, so that a group of aptamers can be found at the end by comparing the affinities in incubation with the target.

In the spatially separate amplification, such as that used here, each oligonucleotide is amplified individually. In the previous amplification, the oligonucleotides also compete with one another in amplification, so that oligonucleotides with an inferior amplification efficiency may be lost, regardless of their binding qualities.

In general, the process steps listed here need not necessarily take place in the order given above. The order may be varied if reasonable and technically feasible. In particular, it is possible to vary the order of the steps performed after step a) bringing a mixture of oligonucleotides in contact with the predetermined aptamer-target structure, and b) binding at least some of the oligonucleotides to the target structure and separating the oligonucleotides that are bound to the aptamer-target structure. For example, the spatially separate amplification, issuance of a specific marker, sequencing and analysis of the binding properties of the aptamer-target structure may take place in different chronological orders, or several of these steps may be performed simultaneously, as is clear from the following discussion and exemplary embodiments.

The steps enumerated above will now be explained in detail.

The term "aptamer" refers to short, single-stranded nucleic acid oligomers, which bind specifically to a target structure or a target molecule, also known as the target, for example, to a protein, to low-molecular compounds such as organic substances, amino acids and antibiotics, nucleic acids, virus particles or (micro)organisms, as well as additional targets, as mentioned in the introduction. The aptamer-target binding takes place as mentioned in the introduction.

The starting substance used in this process is a mixture of oligonucleotides. The term "mixture" refers to a number of oligonucleotides having different sequences.

The oligonucleotides preferably have one or more variable regions, preferably internal variable regions. Furthermore, primer regions may also be present, preferably on the 5' and 3' ends of the oligonucleotides. An internal variable region, one or more of which may be present, is a randomized sequence region, for example, in particular a region, which is or has a combinatory random sequence. An internal variable region has a length of 10-80 nucleotides, preferably 20-80, more preferably 40-80 nucleotides, for example, but these lengths are given only as examples and do not represent a restriction in any way. A region with a fixed sequence may be situated between two variable regions. A non-restrictive example of this is a capture sequence, which will be explained in greater detail below.

Primer regions serve as primer binding sites for amplification, preferably PCR amplification. Alternatively or additionally, the primers may serve to bind the oligonucleotides to a solid phase, for example, plates, beads, chips or other substrates, as will be described further below. Furthermore, additional modifications, such as fluorescence molecules, biotin labels, enzymes, etc., may be introduced via the primers before, during or after the process.

The starting substance, i.e., the starting mixture of oligonucleotides, is also referred to as a library, a starting library, an oligonucleotide library or a combinatory random library. Oligonucleotides having the structure described above can be ordered from commercial providers. The variability of a library is in the range of approx. $10^{15}$ different molecules, for example.

The oligonucleotides may be single-stranded DNA (ssDNA), RNA, modified ssDNA or modified RNA or synthetic nucleic acid-like molecules (e.g., PNA). In the course of the process, complementary strands to the oligonucleotides are present in individual process steps, in particular in the amplification steps. After the end of amplification, the oligonucleotides and their complementary strands are present in the amplicons, which can be used to yield the desired ssDNA for further investigations of target binding. For investigation of target binding, the oligonucleotide single strands, in particular ssDNA, are investigated.

This method is also suitable in particular for use for natural and artificial nucleic acids, in particular for Spiegelmers, synthetic DNA-like molecules (PNA), etc. The principle of the Spiegelmers was explained above.

Bringing the oligonucleotides in contact with the aptamer-target structure, binding at least some of the oligonucleotides to the target structure and separating the oligonucleotides that are bound to the aptamer-target structure from the aptamer-target structure and from oligonucleotides that are not bound to the aptamer-target structure can be accomplished in any of a variety of ways, in particular as is already known from the SELEX processes known in the prior art. A few variants are presented as examples below, although this does not limit the process in any way.

For example, the target may be bound to a solid phase and brought in contact with dissolved oligonucleotides, wherein some of the oligonucleotides, the potential aptamers, bind to the target. The solid phase may have properties that do not allow easy separation from the liquid phase with oligonucleotides not bound to the target. For example, the solid phase may be magnetic, e.g., in the form of magnetic particles (magnetic beads). The target-bound oligonucleotides can be eluted from the solid phase and the target in an elution step, as is already known from the SELEX process.

In another variant, a so-called capture sequence is bound to a solid phase, preferably in the form of magnetic particles. Binding of single-stranded oligonucleotides from the starting library to the solid phase is accomplished by way of the capture sequence. The capture sequence is complementary to a region within the single-stranded oligonucleotides of the starting library. With the help of the capture sequence, a reversible binding takes place between the capture sequence and the oligonucleotides. The target is then present in free form in solution and is available for binding to the oligonucleotides, the potential aptamers. Target-specific oligonucleotides couple by forming a defined two-dimensional or three-dimensional structure of the capture sequence and can be found in solution together with the target. The solid phase to which the non-target-specific oligonucleotides remain bound may then be separated together with these oligonucleotides.

Additional variants include binding methods, which are used in the various modifications of SELEX processes, e.g., binding between whole cells and the oligonucleotide library, then separation of the non-binders by means of centrifugation and elution of the binders by means of heat. An overview of SELEX processes is given by Stoltenburg, R., Reinemann, C., Strehlitz, B. (2007), SELEX—a (r)evolutionary method to generate high affinity nucleic acid ligands, Biomolecular Engineering 24, 381-403.

If the target is bound to a solid phase, there may be a negative selection for the solid phase, i.e., a selection against the solid phase without bound target before the process steps described above.

Selection with other non-specific molecules may also be performed before the process steps described above. Likewise, counterselections may be performed with related, but unwanted, target molecules to deplete the corresponding binders from the oligonucleotide library before the selection.

Spatially Separate Amplification

The term "spatially separate amplification of individual oligonucleotides" has the following meaning: a single oligonucleotide is an oligonucleotide with a certain sequence. All oligonucleotides are amplified in such a way that each individual oligonucleotide is amplified in a spatially separate manner from the others and the resulting amplicon also remains spatially separated from all the other amplicons. Therefore, there is no mixing of the individual amplicons.

An amplicon here comprises a plurality of oligonucleotides, which are obtained by amplification of a single oligonucleotide with a certain sequence. Each amplicon contains primarily and predominantly, depending on the amplification agent and conditions, or exclusively or almost exclusively a type of oligonucleotide with a sequence, which matches the sequence of the single oligonucleotide used as the starting molecule (matrix). The term "type" thus refers to the sequence of an oligonucleotide. A type is marked by a certain sequence. After the amplification step, the amplicon contains strands complementary to the oligonucleotides.

Double strands are also present, depending on the external conditions, such as temperature, pH, salt content, etc. In addition to a certain type of oligonucleotides with an identical sequence, oligonucleotides with a different sequence and corresponding complementary strands that are formed by copy errors in amplification or addition and incorporation of artificial monomers may be present. However, the term "amplicon" in this description is also used for a product from which the complementary strands of the oligonucleotides have been removed, for example, for the purpose of sequencing or for the investigation of target binding of the oligonucleotides. In this sense, the term "amplicon" may also refer to a plurality of single-stranded oligonucleotides, primarily, exclusively or almost exclusively comprising or consisting of a type of oligonucleotide having an identical sequence. Any known amplification process may be used for a spatially separate amplification, but the polymerase chain reaction (PCR) is preferred.

Spatially separate amplification takes place in spatially limited regions in particular, which may or may not be completely closed off. Such limited regions may be created by phase boundaries in particular, such as solid-state structures and fluids or fluid-fluid phase boundaries or fluid-gas phases. Examples include spatially limited cavities, spatial delimitations, which facilitate diffusion in certain directions and impede diffusion in other directions, such as, for example, an arrangement of columns or trenches, porous structures or molecular structures that facilitate and/or restrict diffusion in certain directions, such as hydrogels, aerogels or polymer surfaces, for example. Ordered or unordered nanostructures or molecular structures, such as polymer branches, dendrimers, particle arrays, filter membranes and lipid membranes (spherical or planar) are also possible for implementing spatially limited regions. Likewise, corresponding spatially separate regions may be created by forces and fields or by a combination of phase boundaries and fields/forces, such as electric fields, for example, which restrict diffusion to a certain region or keep the DNA bound to the surface.

In preferred embodiments, the spatially separate amplification is amplification in an emulsion, a digital amplification, an amplification in a cavity or an amplification on a solid phase, in particular an emulsion PCR, a digital PCR or a PCR on a solid phase.

Processes for amplification on a solid phase (solid-phase amplification) are known from the prior art, where randomly distributed amplicons are obtained on a solid-phase surface, for example, a planar surface. Oligonucleotides may be bound to complementary sequences, which are in turn bound to the solid-phase surface, by means of suitable binding sequences through base pairing. The complementary sequences are primer sequences for PCR in particular. Forward and reverse primers for amplification of the oligonucleotides are preferably covalently bound to the solid-phase surface. The required amplification agents for PCR are added. The ratio of primers to templates as well as the duration of the PCR determine the resulting density of the amplicons on the solid-phase surface. With such a process, spatially separate amplicons are obtained on the solid-phase surface as a result. Glass plates are frequently used as the solid phase. Solid-phase amplifications are described in L. Metzker et al., Nature Reviews, Genetics, Vol. 11, 2010, 31-46 and the literature cited therein regarding solid-phase amplification, such as that by M. Fedurco et al., Nucleic Acids Res. 34, e22 (2006), for example.

A known variant of solid-phase amplification is the so-called "bridge amplification," which is available, for example, from Illumina in their SOLEXA sequencer. Suitable forward and reverse primers for the oligonucleotides to be amplified are covalently bound to a solid-phase surface. After binding to the surface, amplification of the oligonucleotides is performed. The newly created complementary strand is covalently bound to the surface and has another binding site on its unbound end. This can then also bind to the fitting primer on the surface and can initiate another amplification, which in turn creates a new oligonucleotide strand bound at one end and having the original binding sequence at its other free end. Exponentially more new strands, which are fixedly bound at one end and whose other end allows an interim binding to the surface, are created. During amplification, a strand is bound tightly (covalently) at one end and loosely (non-covalently) at the other end, and thus creates a molecular "arc," which is also known as a bridge. In this regard, U.S. Pat. No. 6,300,070 describes bridge amplification in general, and Abrams et al., Diagnostic and Gene Detection Ch. (1997), 171-189 describes the use of bridge amplification for sequencing. This process can be expanded by removing the complementary strand after the amplification reaction and performing sequencing and then performing a measurement of binding to the target after sequencing.

If commercially available systems to which certain primer sequences are bound are used for the amplification on a solid phase, then preferably oligonucleotides that are compatible with these primer sequences and/or have binding sites that are compatible with these primers are used in the process according to the invention. If this is not the case, a ligation step is performed with so-called adapters that are compatible with the primers on the solid phase. Optionally the oligonucleotides may also be lengthened accordingly by amplification in terminal position, but this might have an influence on the binding characteristics. It is therefore preferable for the flanking sequences of the oligonucleotides to be compatible with the primer sequences of the commercial sequencing processes.

Amplification in emulsion is preferably an emulsion PCR, preferably using a water-in-oil emulsion as the basis. Droplets of aqueous phase serve as a microreactor. The concentrations of these water-in-oil emulsions are selected, so that, in the ideal case, precisely one oligonucleotide is enclosed in each droplet of aqueous phase. In addition, the required amplification agent, such as primer and polymerase for PCR, are contained in the aqueous phase. After performing PCR, spatially separate amplicons are obtained because the droplets of aqueous phase are present in the oil phase, so that they are separate from one another. Each droplet of aqueous phase preferably contains one type of oligonucleotide and complementary strands. Such a variant of emulsion PCR was described, for example, by M. Nakano et al., Journal of Biotechnology 102 (2003), 117-124 and Williams et al., Nature Methods, Vol. 3, No. 7 (2006), 545-550.

In one embodiment of the invention, the oligonucleotides are bound to solid-phase particles before, during or after the spatially separate amplification, wherein solid-phase particles are obtained with only one amplicon, with one type of oligonucleotide being bound to each. The amplified oligonucleotide or the complementary strand or both may optionally be covalently bound to a particle.

This embodiment may be combined with the variant of emulsion PCR, for example, in which solid-phase particles may also be used in addition to a two-phase system such as water-in-oil. In this variant of emulsion PCR, the oligonucleotides are bound to complementary sequences, which are bound to the surface of the solid-phase particles, via suitable binding sequences. Oligonucleotides are mixed in aqueous phase together with PCR amplification agent and solid-phase particles, which are also known as beads, and are then emulsified in oil, thus forming a water-and-particle-in-oil emulsion. For this water-in-oil emulsion, the concentrations are selected so that, in the ideal case, precisely one DNA strand and precisely one particle are enclosed in each water droplet. Either a primer or a primer pair (forward and reverse) is covalently bound at the surface of the particle. If only one primer (forward or reverse) is bound, the other primer is dissolved in the aqueous phase. If a primer pair is present, then amplification proceeds according to the bridge amplification described above. In the case of bridge amplification on the bead, one of the primers and strands bound covalently by means of the primer (oligonucleotides, complementary strands) are optionally released again after the reaction. As a result, the entire particle can be covered with copies of the original oligonucleotide by amplification in all cases. After amplification, either the oligonucleotides or the complementary strands or both may optionally be covalently bound to the surface. Non-covalently bound oligonucleotides or non-covalently bound complementary strands can be converted to a liquid phase by suitable ambient conditions (salt content, temperature, etc.), and then the covalently bound oligonucleotides or the covalently bound complementary strands remain on the particle as single strands. In the preferred embodiment, a plurality of oligonucleotides is covalently bound to the particle after amplification and removal of the complementary strands. In this special PCR, it is possible to amplify precisely one oligonucleotide, so that it is "copied" a million times onto a small polymer bead. At the end of the emulsion PCR, there are thus a million beads, each of which carries millions of identical copies of another oligonucleotide. Emulsion polymerization and amplification including solid-phase particles (beads) are described by L. Metzker et al., Nature Reviews, Genetics, Vol. 11, 2010, 31-46 and the literature cited therein, such as, for example, D. Dressman et al., Proc. Natl. Acad. Sci. USA (2003), 100, 8817-8822, as well as F. Diehl et al., Nature Methods (2006), Vol. 3, No. 7, 551-559.

If the commercially available systems for amplification in emulsion are used with particles to which certain primer sequences are bound, then oligonucleotides that are compatible with these primer sequences and/or have binding sites compatible with these primers are preferably used in the method according to the invention. If this is not the case, a ligation step is performed with so-called adapters, which are compatible with the primers of the commercially available system, or the nucleotides may be made compatible directly through a suitable choice of primers during PCR. In this case, these primers contain complementary or identical sequences to the commercial system as well as to the oligonucleotide library.

In a digital PCR (dPCR), oligonucleotides are distributed on a large number of spatially separate amplification regions, and PCR is performed separately in each region. In the ideal case, a region contains only either a single oligonucleotide (corresponding to 1) or no oligonucleotide (corresponding to 0). After performing PCR, the regions contain an amplicon of a certain oligonucleotide or no amplicon accordingly. To isolate individual oligonucleotides in separate regions, for example, pico-well plates, micro-well plates, capillaries or arrays of miniaturized cavities or nucleic acid-binding surfaces may be used. PCR in an emulsion, as described above, is also occasionally considered to be digital PCR. The procedure for performing digital PCR is described in U.S. Pat. No. 6,143,496, for example, H. Nagal et al., Anal. Chem. 73, 2001, pp. 1043-1047; F. Shen et al., Lab Chip, 2010, Vol. 10(20), pp. 2666-2672; B. G. Zimmermann et al., Prenat. Diagn., 2008, Vol. 28(12), pp. 1087-1093; Y. Gong et al., Lab Chip, 2010, Vol. 10(18), pp. 2334-2337; S. Lindstrom et al., Lab Chip, 2009, Vol. 9(24), pp. 3465-3471; J. S. Marcus et al., Anal. Chem., 2006, Vol. 78(3), pp. 956-958. Methods and means for performing digital PCR are commercially available from the company Fluidigm, for example.

Issuing a Specific Marker

Each spatially separate amplicon is issued a specific marker, on the basis of which it is unambiguously identifiable. The identification may in principle be performed in any conceivable manner and is in particular an optical, spectroscopic, radioactive or electronic method (e.g., by means of a barcode or an RFID chip) on the basis of the spatial position or the sequence of amplicons that can be detected optically in particular. In one variant, the amplicons, provided with a specific marker, for example, an additional DNA sequence, a mass spectrometer tag or an isotope labeling. When the amplicons are bound to supports, for example, a solid-phase particle, as described above, then preferably a marker or label is present on the support or its position. Due to the fact that the support carrying the amplicon is marked and/or labeled, the bound amplicon is therefore also marked. Possible, but not conclusive, markers include barcodes, color codes, size, shape, spatial position or arrangement, mass spectrometer tags, isotope labeling, DNA labeling.

In another variant, the amplicons are arranged in various locations and the location carries an unambiguous marker, for example, a numbering or location coordinates. In one embodiment, the method comprises the arrangement of the amplicons in locally separate regions in or on one or more first support(s), yielding an array of amplicons, in which a specific location marker is assigned to each amplicon as a specific marker. In this embodiment, the sequencing of the oligonucleotides takes place in multiple amplicons of the array. The sequence of the type of oligonucleotides contained in an amplicon is assigned to the specific location marker of the amplicon in the array. In analysis of the binding properties of the aptamer-target structure, the sequence of the type of oligonucleotides contained in an amplicon and the specific location marker of the amplicon are assigned to a positive or negative binding event. Examples of supports include plates, chips, picowell plates, gels, microarrays, so-called polonies bridge amplification, spatial arrangement of aqueous droplets in an oil, for example, a tube (where one droplet sits behind the other like a string of pearls) or a picowell plate in a collection of micro/pico cavities of a microfluidic chip or a surface (with and without structure).

The arrangement of amplicons at various locations in or on a support may be combined with the method of amplification. In amplification on a solid phase, the solid phase may already be the support, and the amplicons are arranged in a regular or irregular pattern at various locations on the support. In the case of digital PCR, the amplicons may already be bound to the inside walls in the respective cavities or to nucleic acid-binding surfaces present in the cavities, so that the arrangement of cavities as spatial labeling allows an assignment to the sequence.

In the case of an emulsion PCR, the amplicons may be present, for example, in dissolved form in droplets from an aqueous phase or may be bound to solid-phase particles, which are present in aqueous droplets, as described above. The droplets with dissolved amplicon may be distributed and immobilized on a flat support. The droplets may be affixed to the surface of the support by means of a hydrophilic coating in the respective positions, for example, so that they are arranged in a given spatial arrangement on the support. For example, the support may have a regular pattern of hydrophilic spots. The droplets may be separated from one another by an oil phase on the support.

Droplets may also be introduced into the cavities of the support, in particular a micro-, nano- or pico-well plate or a sequencer chip. An emulsion system with binding of the amplified DNA on a chip is described by Q. Ge et al., Molecules 2008, 13, 3057-3068.

In a particularly advantageous embodiment, the amplicons are present on the surface of solid-phase particles according to an emulsion PCR as described above, for example, and the solid-phase particles (beads) with the amplicons are disposed in locally separate regions in or on one or more solid support(s), yielding an array of amplicons. The beads may be arranged in or on a gel, a plate or some other flat support and are preferably immobilized by chemical crosslinking on a surface with chemical functional groups, for example. In a particularly preferred embodiment, the beads are placed in the cavities of a micro- or picowell plate or a sequencer chip, for example, by centrifugation. The dimensions of the beads and cavities are preferably coordinated, so that precisely one bead will fit into a cavity.

Sequencing

As mentioned above, each amplicon contains primarily or predominantly, depending on the amplification agent and amplification conditions, or almost exclusively, one type of oligonucleotides with an identical sequence, which corresponds to the sequence of the single oligonucleotide used as the starting molecule (matrix). So-called sequencing methods are used to decode the sequence of oligonucleotides in the amplicons. Sequencing machines, which use a variety of reaction steps and techniques to first capture oligonucleotides or polynucleotides, in particular the DNA thus obtained, to replicate them and then to output them, building block for building block. By means of the selected reaction chemistry of the sequencing method, it is then possible for each individual cavity to calculate the DNA sequence of the oligonucleotide it contains.

In the method according to the invention, the oligonucleotides are sequenced in spatially separate and specifically marked amplicons. The sequence of the type of oligonucleotide in an amplicon is assigned the specific marker of the amplicon.

Complementary strands to the oligonucleotide that are contained in the amplicon are preferably removed before the sequencing, yielding a product from which these complementary strands have been removed, and which is still referred to as an amplicon for the purposes of the present invention.

Complementary strands can be removed by various methods, which are known to those skilled in the art. In the case of emulsion PCR with beads or solid-phase PCR, as described above, the beads and/or the surfaces have only one primer, for example, and the other primer is added in solution. Thus, the oligonucleotide strand previously obtained by positive binding to the aptamer-target or the complementary strand is optionally anchored on the surface directly by PCR. Other possibilities are available through binding systems, for example, streptavidine-loaded beads and primers with biotin. Single strands can then be generated by washing under denaturing conditions, so that the unwanted complementary strand is simply dissolved. The oligonucleotide strand remains covalently bound to the bead or the surface and cannot be lost. Suitable methods include washing with a highly saline buffer, SSC buffer, dilute sodium hydroxide solution and/or heating.

In the process according to the invention, sequencing techniques in which the amplicons are arranged in locally separated regions in or on one or more solid support(s), also referred to as "templates." To this extent, reference is made to the above disclosure about this aspect. Each amplicon arranged on the support is sequenced separately.

Such sequencing techniques are also referred to here and in the relevant literature as "sequencing techniques of the next generation" or NGS (next-generation sequencing). NGS sequencing techniques may be based on various platforms, some of which are available commercially, for example, from the companies Roche (Roche/454) and Illumina/Solexa, Solid and Ion Torrent. An overview of NGS techniques can be found in L. Metzker et al., Nature Reviews, Genetics, Vol. 11, 2010, 31-46.

NGS technology, such as that used by Roche in the GS FLX 454 system, is based on, among other things, techniques described by Wheeler, D. A. et al., Nature 452 (2008), 872, Shendure, J., Ji, H., Nature Biotechnology 26 (2008), 1135-1145, U.S. Pat. Nos. 7,244,559, 7,323,305, 7,335,762, 7,638,276. Ion Torrents Technology is based on the same amplification and positioning system of the amplicons but it uses a field effect transistor to select the biochemical reactions (J. M. Rothberg, Methods and apparatus for measuring analytes using large scale FET arrays, publication date: May 21, 2009; publication no. US Patent 2009/0127589 A1). The geometry of the arrangement of the amplicons of the two technologies, however, is based on an identical principle and thus allows highly parallel sequencing of up to $10^6$ DNA sequences, each with a length of approx. 500 base pairs, and shorter sequence lengths are also possible. In this technique, beads on the surface of which an markedamplicon of a certain oligonucleotide is bound, are introduced into a sequencer chip. A chip contains millions of small cavities, each of which is large enough, so that exactly one bead fits into each cavity. Then the chip can be filled with smaller beads, which contain all the enzymes for the sequencing reaction. However, this is not absolutely necessary and instead it is a preferred embodiment of the sequencing technique itself. In the sequencing which then takes place, a light signal is generated with the 454 FLX system, an electrical charge is generated by means of $H^+$ ions in the case of Ion Torrent when a DNA base is incorporated. The signal is recorded in parallel for each cavity and thus each bead and may then be converted to a DNA sequence. Thus, a single NGS chip makes it possible to detect up to 1 billion base pairs or even more. The principle of sequencing and the processes taking place in sequencing are explained by M. Ronaghi, Genome Res. (2001), 11, 3-11 and M. Margulies et al., Nature (2005), Vol. 437, 376-380.

As an alternative to the bead-based NGS systems, there are also systems that use bridge amplification (e.g., Solexa). In these processes, the oligonucleotides are bound to a surface in a random distribution and are amplified, so that several times $10^5$ copies of the original oligonucleotide are formed around each binding site. These individual amplification regions are usually arranged in a circular pattern around the original oligonucleotide. In the embodiment of sequencing from Illumina, this spatial arrangement is analyzed by incorporating different fluorescent nucleotides (U.S. patent application Ser. No. 12/878,687, Nucleic Acid Sequencing System and Method). However, an analysis of this special arrangement can also be performed by means of the detection principles of the 454 FLX system or the Ion Torrent system, to derive the sequence from that. Reference is made to the discussion in U.S. Pat. No. 6,300,070, as well as L. Metzker et al., Nature Reviews, Genetics, Vol. 11, 2010, 32-46 and Abrams et al., Diagnostic and Gene Detection Ch. (1997), 171-189. In addition, in this sequencer design, the DNA sequence is often determined by ligation of different fluorescently labeled oligonucleotides. The oligonucleotide library can also be selected here, so that it is accessible to this sequencing and is available for a subsequent binding measurement of the oligonucleotides/aptamers.

Analysis of the Binding Properties

Finally, an analysis of the binding properties of types of oligonucleotides of marked amplicons to the aptamer-target structure is performed. Oligonucleotides having the sequence of the type of the oligonucleotides contained in the amplicons are therefore brought in contact with the aptamer-target structure. In one variant of the process, the spatially separate amplicons can be brought in contact with the aptamer-target structure. It is not necessarily to bring the amplicon itself and oligonucleotides contained therein in contact with aptamer-target structure. The phrase "analysis of the binding properties of types of oligonucleotides" also includes the analysis of oligonucleotides which have the same sequence as the oligonucleotides of a certain type and are thus to be attributed to the type but are no longer present in the marked amplicons. For example, copies of oligonucleotides can be created and analyzed as described below in special embodiments. The phrase "analysis of the binding properties of types of oligonucleotides" thus also includes in particular the fact that oligonucleotides in the amplicons are brought into contact with the aptamer-target structure and/or copies of the oligonucleotides are brought into contact with the aptamer-target structure.

The phrase "assigning the analyzed binding properties to the specific markers of the amplicons" means establishing a relationship of a type of oligonucleotides that has been analyzed to the amplicon, in which that type is to be found with the help of its marker. The sequence of the type of oligonucleotides is known from the sequencing, so that, as a result, an assignment of a binding property to one type of oligonucleotide, its sequence and marker of the corresponding amplicon takes place.

Binding properties can be classified on the basis of a selected defined scale of measured values. A classification may be qualitative and/or quantitative. For example, oligonucleotides that have been analyzed can be ranked from the highest signal to the lowest. A qualitative classification may range from no affinity to very high affinity, for example. Furthermore, a differentiation in quality levels is also possible on the basis of one or more defined limit values. Binding properties can be represented as intensities with relative units in fluorescence and RIfS measurement, among others, as described below.

This method may also be referred to as a method for analyzing oligonucleotides for the purpose of characterization, identification, production and/or selection of aptamers or potential aptamers.

During or after analysis of the binding properties, oligonucleotides are identified as aptamers. The identification may be made on the basis of a classification, such as that described above as an example. Identified oligonucleotides are preferably those having a binding property for the target structure or those in which a binding event is ascertainable.

This method may include a selection step, wherein oligonucleotides identified as aptamers are selected from all the oligonucleotides analyzed.

Oligonucleotides identified as aptamers may optionally be isolated or newly synthesized.

In one variant, the analysis of the binding properties may include in particular:
i) assigning a positive or negative binding event to the specific marker of the amplicon and the sequence of the type of oligonucleotides contained in the amplicon, and
ii) identification of the oligonucleotides in which a positive binding event is detected, as aptamers for the target structure.

A positive binding event can be defined as a certain detectable signal difference in comparison with the base signal and/or a negative control in which there is no binding. In addition, differentiation is also possible beyond the signal level.

Before analysis of the binding properties, complementary strands that are preferably present in the amplicon and are complementary to the oligonucleotide are preferably removed. This step is unnecessary if the complementary strands have already been removed prior to sequencing, as described above.

Analysis of the binding properties can be performed using any of the methods already known from the prior art for aptamers, in particular using methods for determining the affinity of aptamer for target.

A binding event of aptamer to target can be detected with various conventional methods, which are already known from the prior art, in particular from affinity measurements between ligands. If the aptamer is brought into contact with the target, the result is an aptamer-target complex due to binding of the aptamer to the target. The binding and/or binding event can be detected visually, optically, photonically, electronically, acoustically, optoacoustically, by weight, electrochemically, electrooptically, spectrometrically, enzymatically or otherwise chemically, biochemically or physically.

The complex can be visualized by labeling in an indicator reaction, for example, after a direct or indirect coupling of a complex partner with a labeling substance. Either the aptamer used or the target may be provided with a label. Preferred labels are visually, optically, photonically, electronically, acoustically, optoacoustically, electrochemically, electrooptically, spectrometrically, enzymatically or otherwise physically, chemically or biochemically detectable or by weight. In one embodiment of the method, the label is detected by luminescence, by UV/VIS spectroscopy or enzymatically, electrochemically or radioactively.

Luminescence relates to the emission of light. In the method according to the invention, for example, photoluminescence, chemiluminescence and bioluminescence are used for detection of the label. In photoluminescence of fluorescence, absorption of photons leads to excitation. Examples of fluorophors include, without restriction, bis-benzimidazole, fluorescein, acridine orange, Cy5, Cy3 or propidium iodide, which may be covalently bound to aptamers, tetramethyl-6-carboxyrhodamine (TAMRA), Texas Red (TR), rhodamine, Alexa Fluor dyes (including fluorescent dyes of various wavelengths from various companies). The analysis is performed visually or with corresponding measurement equipment, for example, in the multilabel counter, in the fluorescence microscope or by flow-through cytometry, e.g., in the cytofluorimeter. Chemiluminescence describes the emission of visible light as the result of a chemical reaction. Bioluminescence refers to the emission of visible light as a result of an enzyme reaction, for example, a redox reaction catalyzed by the enzyme luciferase.

Other labeling substances are catalysts, colloidal metallic particles, e.g., gold nanoparticles, colloidal non-metallic particles, quantum dots, organic polymers, latex particles or liposomes with signal generating substances. Colloidal particles can be detected colorimetrically.

Enzymes whose enzymatic reaction is characterized by the consumption or formation of detectable substrates or products can also be used as labels, whereby an optical or electrochemical detection may be used without restriction. Detection can be performed, for example, with enzymes as the labeling substances, which convert substrates to colored products, preferably peroxidase, green fluorescent protein (GFP), luciferase, β-galactosidase or alkaline phosphatase. For example, the colorless substrate X-Gal is converted by the activity of the β-galactosidase to form a blue product whose coloration is detected visually.

This detection may also be accomplished by means of radioactive isotopes with which the aptamer is labeled, preferably $^3$H, $^{14}$C, $^{32}$P, $^{33}$P, $^{35}$S or $^{125}$I, especially preferably $^{32}$P, $^{33}$P or $^{125}$I. In scintillation counting, the radioactive radiation emitted by the radioactively labeled aptamer-target complex is measured indirectly. A scintillator substance is excited by the radioactive radiation. In the transition to the ground state, the excitation energy is released again as flashes of light, which are amplified and counted by a photomultiplier.

The aptamers may also be labeled with digoxigenin or biotin, which is bound by antibodies or streptavidine, for example, which may in turn have a label, for example, an enzyme conjugate. The previous covalent linkage (conjugation) of an antibody with an enzyme may be accomplished in various known ways. Detection of the antibody binding may also be performed radioactively in an RIA (radioactive immunoassay) using radioactive isotopes, preferably $^{125}$I, or by fluorescence in an FIA (fluoroimmunoassay) using fluorophors, preferably fluorescein or FITC.

In an especially advantageous embodiment, a label-free detection method based on the so-called imaging reflectometric interference spectroscopy (referred to below as iRIfS) is used for detection of a binding event. This method is based on the fact that the addition of molecules to a surface can be detected by a shift in the interference pattern, based on interference on thin layers. This method can also be used to measure binding kinetics. The principles of this method are described by C. Hanel et al., Analytical and Bioanalytical Chemistry 372 (2002), 91-100, J. Piehler et al., Analytical Biochemistry 249 (1997), 94-102 and in US 2010297671. With the iRIfS method, it is possible to perform a selection of binding reactions on microarrays in real time and without labels. In the present invention, a highly parallel analysis of binding events and the determination of binding constants can be performed. With iRIfS it is possible to ascertain in real time whether and, if so, how strongly and with which kinetic parameters an interaction takes place between the target molecules and each individual amplicon. The binding kinetics and affinity constants of all aptamers on the array can be determined in parallel. Furthermore, parallel investigations of the target affinity can be performed under various conditions (temperature, pH, salt content, etc.) and investigations of specificity may be performed, in which up to $10^6$ amplicons on an array can be analyzed at the same time.

Additional special embodiments and variants as well as additions to the method described above are detailed below:

Bringing oligonucleotides having a sequence of the type of oligonucleotides contained in the amplicons in contact with the aptamer-target structure can be performed in a variety of ways, as described below.

In one embodiment of the method, an array of amplicons is brought in contact with the aptamer-target structure as described above. Amplicons arranged in separate cavities of a DNA chip, a microtiter plate or a microwell plate, for example, may be incubated with a liquid containing the aptamer-target structure.

Creating Copies and Derivatives of the Array

In another embodiment, the method comprises:
creating a copy or a derivative of the array of the amplicons in or on a second support, whereby a specific location marker is assigned to each amplicon of the copy or of the derivative as a specific marker,
brining the copy or the derivative of the array in contact with the aptamer-target structure.

In this embodiment, oligonucleotides or amplicons or derivatives of the oligonucleotides or of the amplicons are copied onto a second support directly from an amplicon array (hereinafter also referred to as "array") in or on a first support, for example, a sequencer chip, wherein the array structure and thus the specific location marker of the amplicons of the array are preserved. The specific location marker, which is assigned to the amplicons on the copy or the derivative is thus based on the specific location marker of the amplicons in the array, which serves as a model. Location information on the copy can be assigned unambiguously to each location position on the original and vice versa.

This embodiment makes it possible in particular to produce a copy of a microarray from an arrangement of oligonucleotide sequences from a sequencing (for example, a particle array in a sequencer from ABI or Roche 454 or a planar surface, such as that from a Solexa from Illumina).

A copy according to the invention may be understood to be a 1:1 copy of the original oligonucleotide, while a derivative may be understood to be a change in the original oligonucleotide, for example, derivatives or subsets of the original oligonucleotides.

In principle, the copy process can be repeated many times, so that a plurality of identical oligonucleotide microarray copies can be produced from a sequencer chip, for example. The original is preserved here. For this embodiment, the aptamer identification and the analysis on many parallel samples are facilitated again because a wide variety of different tests can be performed on the various copies, and new copies can be produced as needed. For example, binding kinetics and the affinity constants of all aptamers can be determined in parallel on copies of the array. Furthermore, parallel tests of target affinity may be performed under various conditions (temperature, pH, salt content, etc.) and tests of specificity. In particular, one copy is analyzed with the label-free iRIfS technique, which was explained above, which permits, among other things, an affinity analysis of all oligonucleotides on the array copy produced.

Before bringing the copy or the derivative of the array in contact with the aptamer-target structure, the complementary strands to the oligonucleotides, which may be present in the amplicons of the copy or of the derivative, are preferably removed. This can be done by known methods, some of which are listed in the "Sequencing" section.

In this embodiment, the second support in particular has a binding adapter for oligonucleotides or binding properties for oligonucleotides, and the copy or the derivative is created by binding oligonucleotides from the amplicons to the support by means of the binding adapters or the binding properties. Binding adapters are preferably oligonucleotides, most preferably with the length and function of a primer for PCR. Binding adapters preferably have sequences that are complementary to some of the sequences of the oligonucleotide complementary strand and/or that contain sequences identical to the oligonucleotide. In amplification performed on the second support, the binding adapter may be lengthened to form an oligonucleotide strand that is covalently bound to the surface of the second support. The oligonucleotide thereby created may be identical or complementary to the original oligonucleotide. Binding adapters may also have sequences that are complementary to some of the sequence of the oligonucleotide strand. In amplification performed on the second support, the binding adapter may be lengthened to an oligonucleotide complementary strand that is covalent bound to the surface of the second support.

This embodiment also makes it possible to copy amplicon arrays even without knowledge of the biochemical information or the sequence. This makes it possible make a copy of the arrangement of oligonucleotides there before, during or after a sequencing process and to thereby create an array copy without having knowledge of the sequences. Only the assignment of the location information to the copy must allow an assignment to the sequence information of the sequencer system.

This embodiment thus makes it possible to produce an array copy immediately before, during or after the sequencing described above, even without knowledge of the sequences of the individual oligonucleotides. It is thus possible to sequence the copy produced in this embodiment to determine the identity of the aptamers in the copied amplicons. Thus the same steps in principle may be performed as on the array original. The sequencing may be performed with the original or the copy before, during or after preparation of the copy.

According this embodiment, a copy or a derivative may be produced before, during or after the sequencing or amplification, or a copy may in turn serve as an original for sequencing. The binding of the copies or derivatives to the second support preferably takes place simultaneously or after amplification. The copy or the derivative may be produced before amplification, for example, by using the Solexa system from the company Illumina. Further amplicons of the original oligonucleotide are created here before, during or after amplification and then are transferred to a second support. Based on the original oligonucleotide, both complementary and identical amplicons can be transferred. This second support may be, for example, a sequencer chip of a 454 from Roche. It is also conceivable to make a copy after sequencing using the 454 system from Roche and to then feed this into a Solexa sequencer and sequence it again.

A special variant of this embodiment comprises the following steps:
  providing at least one spatially limited amplification agent region for each oligonucleotide which is separated from the amplification agent regions of the other oligonucleotides, such that a surface of the second support, which is provided with the binding adapter or binding properties, is adjacent to the amplification agent regions,
  amplifying the oligonucleotides by means of amplification agent regions in the amplification agent regions for creating amplicons of the oligonucleotides,
  binding single strands of the amplicons or derivatives of the amplicons to the second support by means of the binding adapter or the binding properties, so that a spatial arrangement of the single strands on the second support corresponds to the spatial arrangement of the amplicons in the array from which the single strands originate, and
  removing the second support with the bound single strands from the array.

The spatially limited amplification agent regions may be defined at least in part by micro- or nanostructures in the first support, which carries the array or in the second support, which carries the copy or the derivative:

Amplification according to the above embodiment may be identical to the spatially separate amplification, as described above, on the basis of the general process. In this case, the spatially separate amplification takes place in the amplification agent regions.

Amplification according to the above embodiment may also be an additional (e.g., second) amplification step, which is performed after the spatially separate amplification that was described above on the basis of the general process. For example, it is possible for beads which carry a plurality of covalently bound oligonucleotides after an initial spatially separate amplification and removal of oligonucleotide complementary strands to be brought in contact with an amplification agent in the amplification agent regions, leading to synthesis of an oligonucleotide complementary strand in the amplification. Amplification according to the above embodiment may thus be equivalent to synthesis of complementary strands. The phrase "amplicon of the oligonucleotides" in this case includes the complementary strands. By a different choice of primer, it is also possible to create oligonucleotides identical to the original oligonucleotide as the amplicon.

The single strands of the amplicons that are bound to the second support may be single strands in the oligonucleotide and/or their complementary strands, preferably the complementary strands. The binding preferably takes place by hybridization of oligonucleotide single strands and/or their complementary strands to the binding adapter with a sequence.

A binding adapter at the surface of the second support preferably has a sequence, which is complementary to a portion of the sequence of the oligonucleotide complementary strand. Complementary strands bind to binding adapters by hybridization. Then a further amplification is preferably performed on the second support in which the binding adapter is lengthened to an oligonucleotide strand. The result then obtained is oligonucleotides covalently bound to the surface of the second support. This additional amplification step may be performed before or after removing the second support. Complementary strands that are no longer needed can be removed by the usual methods (washing with buffer, heating) as already mentioned.

In one variant, creation of at least one spatially limited amplification agent region for each oligonucleotide includes supplying the oligonucleotides in separate assigned recesses in the support which carries the array, introducing the amplification agent into the recesses and sealing the recesses with the second support. For example, the second support may be a flat support, which is placed on a first support with cavities such as a microwell plate or a picowell plate, wherein the oligonucleotides to be amplified are to be found in the cavities (for example, in digital PCR, as described above). The second support closes the cavities, forming closed amplification agent regions. The required amplification agents are present in the cavities and a copy of the amplicons is preferably formed on the second support at the same time during amplification. The second support may be a flat support, and a copy in the form of a planar array may be produced there. Such a procedure is described in WO 2010100265, for example. In one variant of this, beads with an oligonucleotide of a certain sequence bound on the surface are present in cavities in a first support and the second support, as a flat support, is placed on the first support, which has cavities. Next, an amplification is performed, while at the same time a copy is created on the second support. One embodiment is described in WO 2010100265 with reference to FIGS. 1a to 1d there.

In another variant, creating at least one spatially limited amplification agent region includes providing the second support with at least one recess assigned to each oligonucleotide, where the binding adapter is arranged, introducing the amplification agent into the recesses and sealing the recesses by means of the first support, so that the oligonucleotides are exposed to the amplification agent region. One embodiment is described in WO 2010100265, with reference to FIGS. 4a to 4c there.

In another variant of this embodiment, the spatially limited amplification agent regions are separated at least partially by phase boundaries between two liquids, a liquid and a gas or a physical boundary. It is also conceivable to provide emulsion droplets on the first support, such that each droplet contains an oligonucleotide of a certain sequence and amplification agent, as described above with reference to emulsion PCR. The droplets can be affixed to the respective positions on the surface of the first support by means of a hydrophilic coating, so that they are arranged in a given spatial arrangement on the support. For example, the support may have a regular pattern of hydrophilic spots. The second support is pressed onto the first support, so that it comes in contact with the droplets at the surface, which preferably has binding adapters. In amplification in the droplets, a copy is produced on the second support at the same time. One embodiment is described in WO 2010100265 with reference to FIGS. 5a through 5d there.

During various copy steps, it is possible to produce modifications of the arrays in chemical form, which contain, for example, certain labels or sequences comparable to a color copy, in which only the yellow component is copied.

Additional aspects of this embodiment are explained in WO 002010100265, the disclosure of which is herewith referenced to the full extent.

Additional Process Steps with an Array Copy, Recovery and Selection

In a supplement to the previous embodiment, this process comprises recovery of one or more types of oligonucleotides from a copy by removing the oligonucleotides from the first support, the second support or a copy of these supports. Copies of the supports include additional copies obtained from an array in or on a first support or copies obtained from the copy on the second support using the copy method already discussed above. However, a preferred embodiment provides for the use of second supports, in particular the DNA copies of a sequence. In this embodiment the oligonucleotides or their amplicons are immobilized, so that they can be released with spatial resolution. With a copied DNA array on a second support, this can be implemented by using photolinkers, so that the oligonucleotides there are partially bound but can be released by using a short-wavelength laser. After the binding analysis by means of iRIfS, for example, an aptamer can thus be released and eluted in a targeted manner by use of the laser. The eluate is then immediately available for additional steps such as PCR. The aptamer can thus be amplified directly and need not be synthesized de novo again. If "epitope binning" is provided, as described in greater detail below, recovered aptamers can be tested as secondary aptamers and thus its binding partners for a sandwich structure can be identified directly.

If multiple aptamers are each released at the same time, this aptamer pool also allows the use of an additional selection step (binding of the aptamer pool to the target, removal of the non-binders, elution of the binders from the target), in particular in conjunction with a mutation of the pool. However, each sequence may be added to the pool or contained in it in a targeted manner. There is thus a significantly greater influence on the aptamer pool for the next selection step than was possible with the previous SELEX process.

In a further supplement to the previous embodiment, this process also comprises the production of additional oligonucleotides by amplification of oligonucleotides of the copy, which are bound to the second support. The copied arrays carry all the aptamers on the surface. Because of the copy producing process, it is now possible to perform PCR on the surface of the array and thus in turn to obtain an aptamer pool for the next round and then also to mutate this one. By selection of suitable primers for PCR, it is also possible to obtain sub-pools of oligonucleotides.

In another supplement to the previous embodiment, it is possible to recover soluble complementary DNA with respect to the aptamers formed during the copy process and to amplify them. This again creates a pool of all the aptamers introduced into the sequencing. Through a suitable choice of primer, it is possible to recover the aptamers as ssDNA in a targeted manner. This pool is then available for an additional SELEX round and can also be mutated to thus create a new library again.

In yet another supplement to the previous embodiment, sub-pools of aptamers are obtained from the copy or the supernatant of the copy process. Since the sequences are known because of the sequencing, it is possible to amplify individual sequence patterns by means of suitable primers in a targeted manner. This is possible by using the supernatant of the copy process as well as the DNA array created. Thus individual sub-pools of the aptamer sequenced originally can be created.

Additional Selection Step

In another embodiment of the process, the amplicons are bound to solid-phase particles, and the process additionally comprises the following steps:
bringing the solid-phase particles, each of which has an amplicon with one type of oligonucleotide bound to it in contact with aptamer-target structure,
ascertaining a positive or negative binding event of the aptamer-target structure to oligonucleotides of the amplicon, which is bound to a solid-phase particle,
selection of solid-phase particles in which a positive binding event can be ascertained.

The selected solid-phase particles in which a positive binding event can be ascertained may be arranged in locally separate regions in or on one or more solid supports, yielding an array of amplicons. The term "selection" means in particular the separation of the solid-phase particles, in which a positive binding event can be ascertained from other solid-phase particles.

However, the solid-phase particles may also be arranged in or on a solid support even before performing the above process steps and may form an array. The term "selection" then means in particular that additional process steps such as the sequencing described below are performed only with solid-phase particles in which a positive binding event can be ascertained.

As described above on the basis of the fundamental process, a mixture of oligonucleotides is brought in contact with an aptamer-target structure, and at least some of the oligonucleotides are bound to the target structure. The oligonucleotides that are bound to the aptamer-target structure are next separated from the aptamer-target structure and from oligonucleotides not bound to the aptamer-target structure. This is a selection process that resembles a SELEX process in which the target is preferably immobilized and the oligonucleotides are present in solution. Because of this selection, it may be assumed that the DNA of each of the solid-phase particles (beads) to which the amplicons created from the selected oligonucleotides are bound has an affinity for the target. However, if the oligonucleotides in the SELEX-like selection have been tested against the immobilized target end solution, the binding of the aptamers to the beads may have altered the affinity. To determine whether this is the case, the additional selection step included in this embodiment (also referred to as "proof selection") is advantageous because the beads are incubated with the target, and then those beads in which a positive binding result can be detected are selected. Next, in additional processes for sequencing and the following steps, only those beads that also bind to the target in this additional selection step are taken into account.

With this embodiment, the quality of the binders is improved and the non-binders are sorted out again. With this optional step, the affinity of the aptamers already selected can be selected again and thus improved, i.e., optimized in a desired direction. Due to the possible double selection, first free aptamer versus bound target and then bound aptamer versus free target, a higher hit rate for aptamers can be achieved, which thus bind their target both in immobilized form and in unbound form in solution. Furthermore, there is a better assurance that the aptamer will bind both the immobilized target and the target that is present freely in solution.

Different embodiments of the proof selection are conceivable, and a few of them are listed below:

A simple estimate of affinity based on the fluorescence of the bead can be performed by using a fluorescently labeled target. This can be done with a FACS machine (e.g., fluorescence-assisted cell sorting). Then the beads may be divided into pools with different fluorescence and these pools can then be sequenced separately to obtain aptamers with different binding abilities.

When the target is immobilized on small magnetic beads, oligonucleotides may be bound to the target. Then a magnetic separation can be performed. Only amplicon beads that bind to the immobilized target will interact with the magnetic beads and then be separated. Pools may also be formed in regions of differing affinity by means of separation at different magnetic field strengths.

In addition, competitive approaches are also conceivable, in which a target and a similar molecule are used, for example, and then a selection is performed for the same or different affinities. For example, if the target is labeled with green fluorescence and the similar molecule is labeled with red fluorescence, then the differentiation may be: only target binding (green), only similar molecule binding (red) and binding both (yellow) beads and thus aptamers.

Selection according to on/off kinetics is also conceivable. This is done by incubating the beads briefly and then measuring them immediately (fast on-kinetics are crucial for high intensity of the fluorescence) or incubating for a long time at a high concentration, washed intensely and for a very long time and then measured (slow off-kinetics are crucial for high intensity of the fluorescence).

Identification of Aptamer Binding Pairs

The process according to the invention can be supplemented by additional steps, which serve to identify aptamer binding pairs. The invention thus also relates to a method for identification of aptamer binding pairs, which bind to an aptamer-target structure in various locations, comprising the steps of the process described above and additionally comprising:

a) bringing the array of the amplicons or the copy of the array of the amplicons in contact with the aptamer-target structure and binding the aptamer-target structure to oligonucleotides contained in amplicons of the array/the copy of the array, b) bringing the array or the copy of the array obtained in step a) in contact with a mixture of oligonucleotides and binding at least some of the oligonucleotides to the aptamer-target structure, which is already bound to the array, c) elution of oligonucleotides that are not bound to the aptamer-target structure in step b), d) removing the oligonucleotides bound in step b) from the aptamer-target structure, e) sequencing the oligonucleotides obtained in step d) and producing or isolating the oligonucleotides in apure type form, f) bringing an array of the amplicons or the copy of the array of the amplicons in contact with the aptamer-target structure and binding the aptamer-target structure to oligonucleotides present in amplification of the array/copy of the array, g) bringing the array of the copy of the array obtained in step f) in contact with a pure type oligonucleotide from step e) and the binding of the oligonucleotides to one or more aptamer-target structures that are already bound to the array, h) analyzing on which aptamer-target structure(s) on the array the pure type oligonucleotide has bound and assigning the target structure to the oligonucleotide of the array to which it is bound and its specific location marker in the array, i) optionally repeating steps g) and h) one or more times.

This method is also referred to as "epitope binning." A sandwich assay with aptamers is performed in this method. Two aptamers that bind to different functional groups ("epitopes") of the target are identified.

By representing all potentially binding aptamers on a surface, it is possible to discover aptamer pairs that bind the target to different functional groups in a targeted manner. These aptamers can then be used in a sandwich assay. Previous methods have not allowed such a highly parallel analysis of binding pairs.

The mixture of oligonucleotides used in step b) can be obtained by recovery from an aptamer copy as described above.

Monitoring of the binding by means of the iRIfS technique described above is advantageous but not absolutely necessary. Therefore, the array (with the immobilized aptamer) or the copy thereof is first incubated with the target to form an aptamer-target complex. Then all the binders can be identified by means of iRIfS.

Next the array is coated with an aptamer pool, preferably from a recovery. Suitable aptamers of the pool can bind as secondary aptamers to the location of the aptamer-target complex, where a free functional group is still present. The binding of secondary aptamers can be determined by means of iRIfS. Then the surface is washed to remove the non-binders. In an elution step, the secondary aptamers are then dissolved and subjected to a sequencing again. Thus, one has all the sequences of the primary aptamers and the sequences of the secondary aptamers. The respective sequences of the secondary aptamers are produced individually. Then a copied array is again incubated with the target and incubated with the secondary aptamers. It is thus possible to find the suitable and fitting primary aptamer for each secondary aptamer and to derive a binding partner for the target therefrom. By means of iRIfS, it is again possible to investigate the kinetics or behavior under various conditions and thus again select aptamer pairs having the desired properties.

Arrays and their Uses, Device

In another aspect, the invention relates to an array of amplicons, as described above, each of which contains one type of oligonucleotides, or a copy of an array of amplicons, each containing one type of oligonucleotides, obtainable according to the method described above, wherein the oligonucleotides are aptamers. In particular the oligonucleotides have one or more variable regions and primary regions, as already described above with reference to the process according to the invention.

Additional aspects of the invention relate to the use of such an array or a copy of such an array for analysis of the binding properties of aptamers to an aptamer-target structure for identification of aptamers for a predetermined target structure or for identification of aptamer binding pairs that bind to different locations on a predetermined aptamer-target structure. Methods of identifying aptamers and aptamer binding pairs were discussed previously in this description.

Finally, the invention also relates to a device for producing aptamers, comprising a unit for bringing a mixture of oligonucleotides in contact with an aptamer-target structure and for binding at least some of the oligonucleotides to the target structure, a unit for separating the oligonucleotides which have bound to the aptamer-target structure, from the aptamer-target structure and from oligonucleotides not bound to the aptamer-target structure, a unit for spatially separate amplification of individual oligonucleotides that are bound to the aptamer-target structure and for obtaining a plurality of spatially separate amplicons, wherein each amplicon preferably contains one type of oligonucleotides, a unit for issuing a specific marker to a plurality of the spatially separate amplicons, so that each of the marked amplicons is unambiguously identifiable on the basis of its specific marker, a unit for sequencing oligonucleotides in a plurality of marked amplicons and a device for assigning the marker specific for an amplicon to the sequence of the type of oligonucleotides in the amplicon, a unit for analyzing the binding properties of types of oligonucleotides to the aptamer-target structure and for assigning the analyzed binding properties to the specific markers of the amplicons and the sequences of the types of oligonucleotides.

The device may also be designed and may have such equipment so that it is suitable for performing all the embodiments described above and all the supplementary steps of the process. Exemplary embodiments of the process according to the invention were described above. Exemplary embodiments of corresponding equipment and/or device for implementing the process steps according to the invention are derived from the description or they will be obvious for those skilled in the art. Therefore, there need not be any further explanation of the fact that a device according to the invention may have suitable handling equipment for positioning the physical entities, e.g., the various arrays, supports or substrates as needed. Furthermore, no further explanation is needed for the fact that suitable fluid equipment may be provided for supplying the respective liquids and/or agents to the required positions. Furthermore, it will be obvious for those skilled in the art that a corresponding control may also be provided to control the device to implement the method according to the invention. Equipment, for example, temperature sensors, may also be provided for creating the environment required for performing the methods.

The invention is described below on the basis of exemplary embodiments.

1. Description of the Method

One example of a preferred method is described below with reference to FIG. 1.

Preparation: Design of the Oligonucleotide Library:

An oligonucleotide library, which is compatible with Next Generation Sequencing (NGS), is preferably designed. The primer regions of the library are selected to be compatible for sequencing (NGS) to enter target-binding ssDNA oligonucleotides directly into the sequencing process by means of NGS. This oligonucleotide library can be used for various processes (e.g., for various targets).

Selection of Aptamers for an Immobilized Target

In a binding step 4, an oligonucleotide library 1 consisting of approx. $10^{15}$ different ssDNA molecules is brought in contact with a target 2, which is immobilized on a target bead 3. Individual oligonucleotides can be bound to target molecules and thus to the target beads 3 in this way. The oligonucleotides 1' with little or no binding to target molecules are then removed by a washing step 5. An RNA oligonucleotide library may also be used as an alternative to an oligonucleotide library of ssDNA.

Elution of the Bound Oligonucleotides from the Target

The remaining bound oligonucleotides are released from their target binding and thus from the target beads 3 by a suitable elution step 6.

Creating Oligonucleotide Beads by Means of Emulsion PCR

The eluted oligonucleotides 7 are subjected to an emulsion PCR 9. First, each oligonucleotide is copied onto precisely one bead 10 and then reproduced. One bead 10 carries the oligonucleotide 7a, another bead 10 carries the oligonucleotide 7b, yet another bead 10 carries the oligonucleotide 7c and still another bead 10 carries the oligonucleotide 7d. The beads carry covalently bound adapter sequences (not shown) which are identical for all beads and to which the oligonucleotides bind by means of base pairing. In the selected diagram, two beads 10 carry the oligonucleotide 7d, which was present many times in the pool. The deciding factor is that each bead 10 carries only a certain oligonucleotide. An oil emulsion is used to achieve the result that one oligonucleotide strand and one bead are enclosed in each case. After PCR, each bead has 10 million copies of exactly one oligonucleotide, so in the schematic diagram shown here, there are four to six copies of an oligonucleotide for each bead 10. The result is a pool of oligonucleotide beads 10. DNA can be replicated a million times on the bead. If an RNA oligonucleotide library was used, a reverse transcriptase emulsion PCR is performed.

Depending on the bead used, optionally a forward primer or a reverse primer may sit on the bead. In the case of a 454 from Roche, this is the sequencer adapter A or B.

In the embodiment shown here, an additional optional binding step 11 and a selection step 8 (proof selection) are performed. In the binding step 11, the target 2 which is dissolved with the oligonucleotides 7 and carries a fluorescence label 12 is added to the beads 10. The labeled target binds only to some of the oligonucleotides, namely to oligonucleotides 7b, 7c and 7d in the schematic diagram selected here, but not to 7a. In selection step 8, the beads 10 with the oligonucleotides 7b, 7c and 7d and the bound target 2 are selected.

Sequencing the Oligonucleotide Beads

The selected oligonucleotide beads with the oligonucleotides 7b, 7c and 7d are fed into a next generation sequencing process. For sequencing, the beads in the filling step 13 with additional smaller beads (not shown) are added to the cavities 15 of a picowell plate 14, referred to here as a chip. The small beads carry an enzyme system, which produces light on incorporation of DNA building blocks in the following sequencing steps 16. The light signal is quantitative for the number of DNA building blocks incorporated. The chip 14 is shown as enlarged like a honeycomb. Each honeycomb cell represents a cavity 15, which is coupled to an optical fiber (not shown, diameter approx. 45 µm) and contains a bead with oligonucleotide. As a result, this yields the sequences of all the oligonucleotides of the pool selected in the selection step 8.

The high-throughput sequencing technique is a next generation sequencing technique, in this case using a 454 sequencer (Roche). Alternatively, other sequencers such as those from Illumina, Solexa, Solid, Ion Torrent, ABI, etc. may be used.

Copying the Oligonucleotides of the Sequencer Chip to an Oligonucleotide Array

By means of the DNA-to-DNA copying technique, the oligonucleotides of the selected pool are copied from the sequencer chip to a planar support 18 in a copy step 17 in the form of an array 20. The array 20 on the support 18 contains all the sequenced oligonucleotides, namely here 7b, 7c, 7d, for example. It is thus possible to create up to $10^6$ spots (shown as 19) with initially double-stranded DNA. Through corresponding workup steps, ssDNA is produced and thus DNA that is functional for target binding is produced, wherein each spot 19 carries the uniform sequences of a selected oligonucleotide. The copy step is explained in greater detail below with reference to FIGS. 2-5.

Measurement and Analysis of the Resulting Array

Next, an analysis of the binding of all the oligonucleotides of the array 20 for the corresponding target is performed in step 21. For an initial overview, the measurement can be performed with a fluorescent target, for example. Binding aptamers can then be identified by their increased fluorescence.

In the preferred embodiment, the binding is detected by means of the iRIfS technique explained in the general description; the performance of this technique is described in C. Hanel et al., Analytical and Bioanalytical Chemistry 372 (2002), 91-100, J. Piehler et al., Analytical Biochemistry 249 (1997), 94-102 and US Patent 2010297671. It is thus possible to ascertain in real time and without labeling whether and how strong and with which kinetic parameters there is an interaction between the target molecules and each individual DNA spot. The binding kinetics and affinity constants of all the aptamers on the array are determined in parallel. Furthermore, parallel tests of the target affinity can be performed under various conditions (temperature, pH, salt content, etc.) and tests of specificity may be performed, in which up to $10^6$ DNA spots on the array are analyzed at the same time.

Assignment of Aptamer Sequences

The affinity constants of the individual oligonucleotides are evaluated comparatively. Aptamers are the oligonucleotides with the highest affinities for the target. Their sequences can be derived immediately from the results of sequencing step 16 because the DNA-to-DNA copying technique ensures that, in step 17, the aptamer spots 19 of the aptamer array 20 are situated in the same positions as on the sequencer chip 14. This provides an unambiguous assignment between binding and sequence.

2. Copy Step

The copy step 17 used in the above example is explained in greater detail on the basis of additional exemplary embodiments a) and b) with reference to FIGS. 2A-2D, 3, 4 and 5.

Exemplary Embodiment a) (FIGS. 2A-2D, 3, 4)

The reference numerals for identical objects are the same as those used in FIG. 1.

Figure 3:
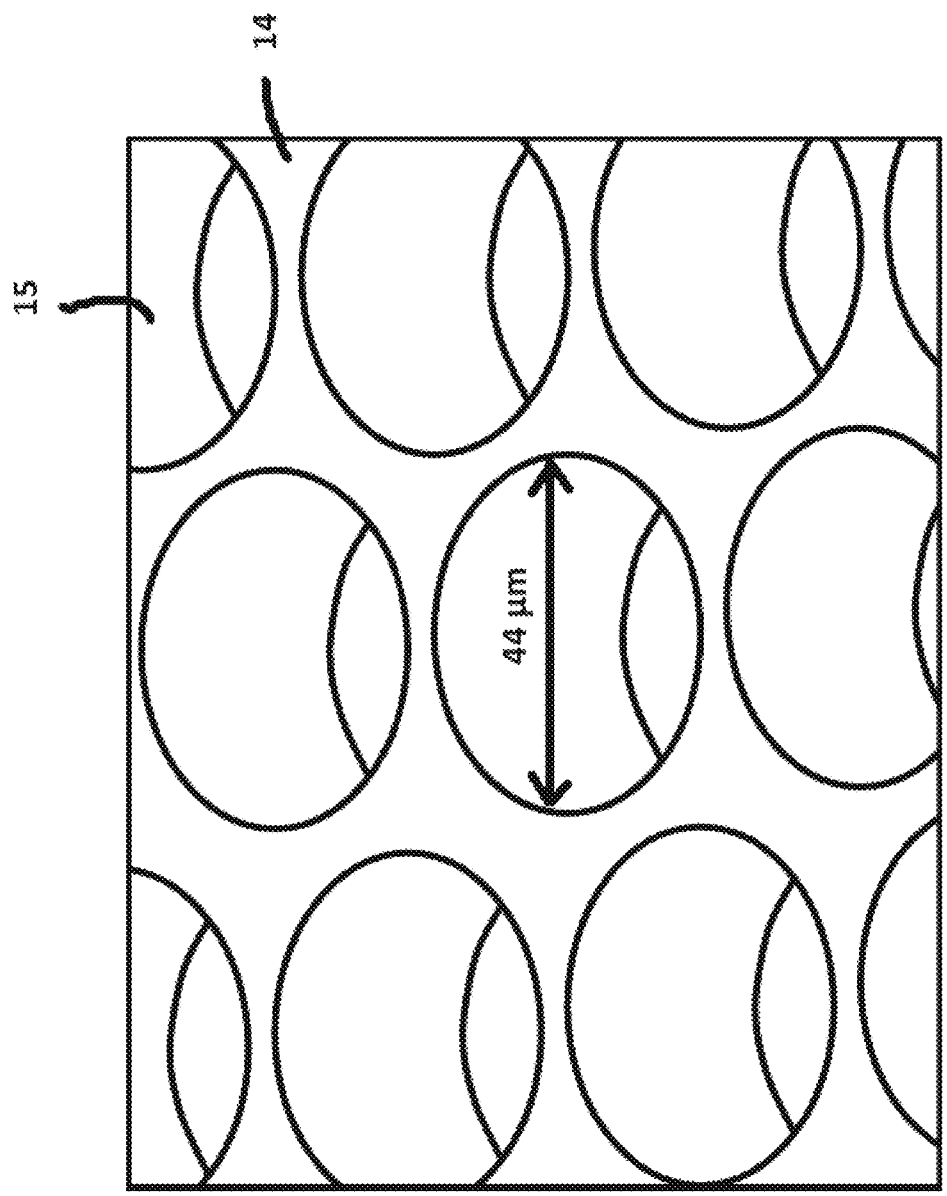
FIG. 3 shows a schematic top view of a detail of the sequencer chip 14 (first support) with microcavities 15.

The sequencer chip 14 has a plurality of microcavities 15. FIG. 3 shows a schematic top view of a detail of the sequencer chip 14 (first support) with microcavities 15. The microcavities may have a dimension of 44 µm, for example, as shown in FIG. 3. This sequencer chip may be, for example, a sequencer chip (GS titanium 2005 and GS FLX titanium 2008) of the 454 sequencer from the company Roche.

Figure 4:
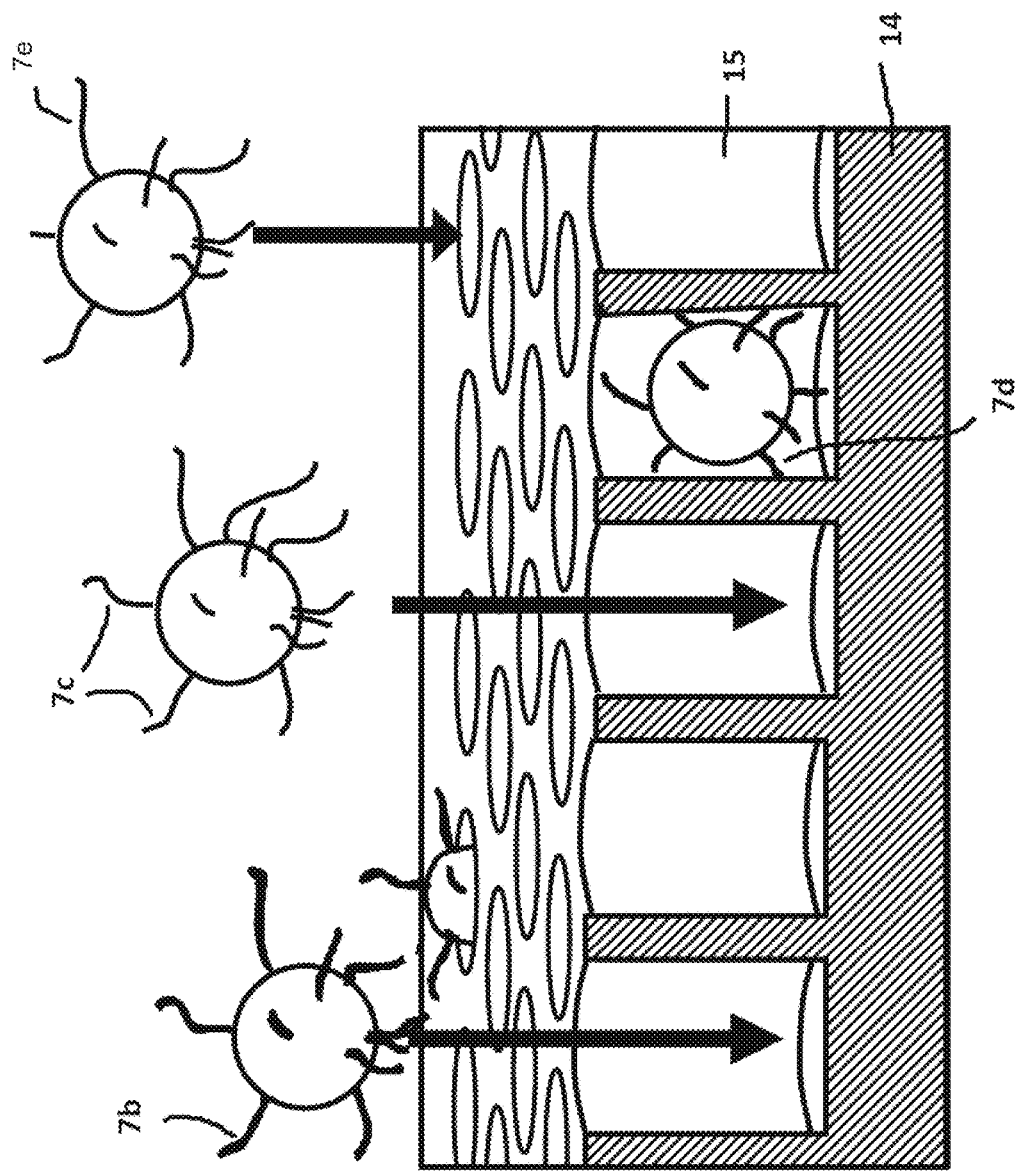
FIG. 4 shows a schematic cross-sectional diagram of the sequencer chip 14 with the cavities 15, into which the particles 10 with the oligonucleotides 7b, 7c, 7d, 7e are introduced.

A particle 10 is placed in each of the cavities 15, each of these particles having millions of copies of one oligonucleotide each 7b, 7c, 7d (cf. FIG. 1) and 7e (not shown in FIG. 1). The plurality of copies is obtained by emulsion PCR, which is a spatially separate amplification, as explained on the basis of the previous example. FIG. 4 shows a schematic cross-sectional diagram of the sequencer chip 14 with the cavities 15, into which the particles 10 with the oligonucleotides 7b, 7c, 7d, 7e are introduced.

In the exemplary embodiment illustrated in FIGS. 2 to 4, this chip is used as the primary array for producing a copy. The oligonucleotides from the cavities 15 are to be copied out of them. The cavities are first filled with an amplification agent for this purpose, for example, a PCR mix. Then, as shown in FIG. 2, a support 18 (second support) is applied, closing the cavities 15 and carrying binding adapters which fit with the amplification agent and are shown schematically as spots 22 in 2b. After closing the cavities 15 with the cover 18, a spatially limited amplification region 24 is thus created for each sample, i.e., each particle 10 with the DNA strands 7b, 7c, 7d, 7e bound to it and this amplification region is separate from the amplification regions 24 of the other samples. The binding adapters 22 are adjacent to these amplification regions 24. In this example, the binding adapters 22 are primers that hybridize with the complementary strands to form the oligonucleotides 7b, 7c, 7d, 7e. These primers 22 are also binding sites for the DNA polymerase. FIG. 2b already shows the state after the amplification step (the second amplification step here after emulsion PCR, which is already performed and in which beads with a plurality of oligonucleotides are obtained, see above) in which complementary strands 7b', 7c', 7d', 7e' of the oligonucleotides 7b, 7c, 7d, 7e are produced. These complementary strands are represented as dotted lines 7 in FIG. 2b. Complementary strands 7b', 7c', 7d', 7e' represent a negative copy of the oligonucleotides.

Figure 2A:
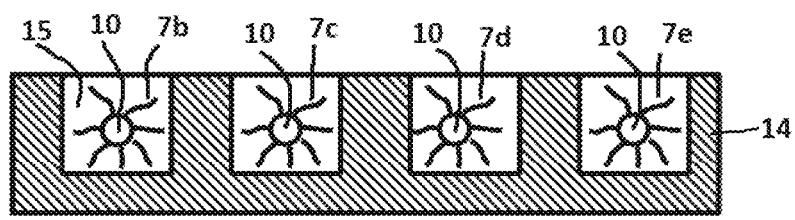
FIG. 2A-2D.
Figure 2B:
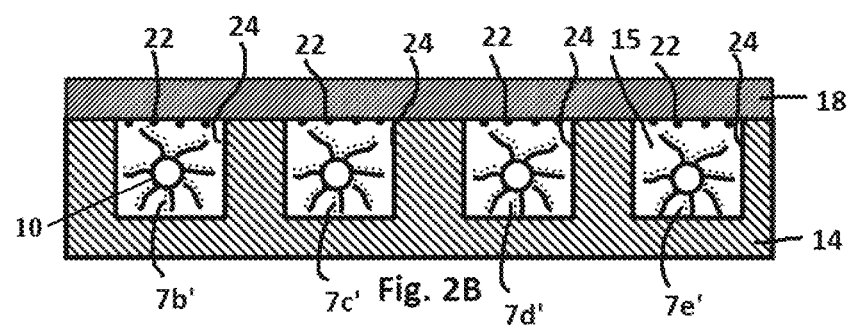
Figure 2C:
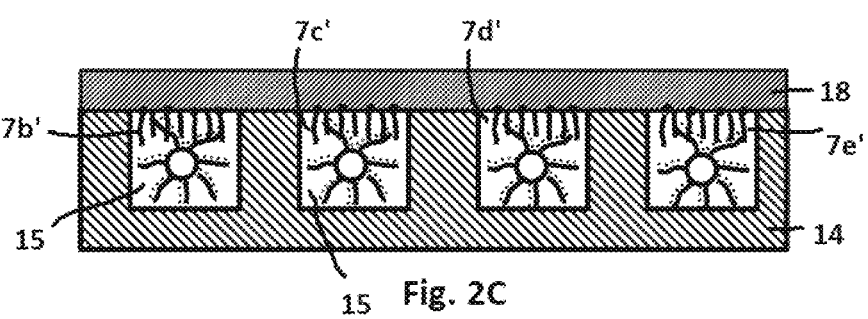
Figure 2D:
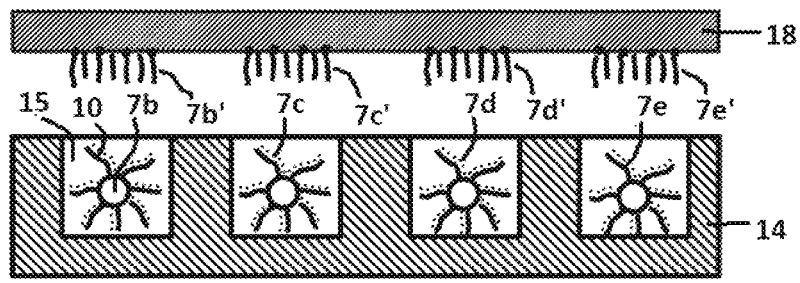

The negative copies 7b', 7c', 7d', 7e' of the oligonucleotides are then released from the particles 10, which can be accomplished, for example, by heating the sequencer chip and thus the cavities in which these are situated. Next, the released copies 7b', 7c', 7d', 7e' hybridize with the binding adapters 22, which can be supported by cooling the sequencer chip, for example. The results of deposition of the copies 7b', 7c', 7d', 7e' on the binding adapters 22 and thus the support 18 is illustrated in FIG. 2c. In this step of transfer of negative copies to the support 18, the location information and/or the recording are preserved because a spatially limited amplification region 24 is provided for each sample and the amplification regions 24 are separated from one another.

Next the support 18 with the negative copies 7b', 7c', 7d', 7e' bound to it is removed from the sequencer chip 14 and contains a negative copy of the array of the nucleotides 7b, 7c, 7d, 7e in the cavities 15 of the sequencer chip 14. The support 18 with the negative copies 7b', 7c', 7d', 7e' may be subjected to another amplification step to again obtain positive copies 7b, 7c, 7d, 7e, which are obtained by lengthening the primers 22. Such a procedure is described in Example b), which follows.

on the basis of the oligonucleotide 7b. The cavities are filled with PCR mix containing soluble primer 30 (b) and closed with a cover 18 (second support) (c) which carries an adapter molecule 22 (fixed primer). The enzymes in the PCR mix first create a negative copy 7b' of the oligonucleotide 7b on the bead in step (d), and this negative copy is then dissolved by heating (e). The negative copy 7b' binds to the binding adapter 22 of the cover by means of a cooling process (f), and in step (g) the enzymes create a fixedly bound negative copy 7b of the negative copy, i.e., a positive copy 7b of the original oligonucleotide 7b. At the end of the process, the cover 18 is removed and now a copy (h) of the array (i) is situated on the cover. The non-covalently bound negative copies 7b', 7c', 7d', 7e' can be removed in a washing step (not shown). Next the copy of the array on the support 18 is used for target-binding experiments.

The original (i) is not consumed in the process; it can be washed and filled again with a PCR mix and reused, e.g., to repeat the process and produce additional copies.

```
                        SEQUENCE LISTING

<160> NUMBER OF SEQ ID NOS: 3

<210> SEQ ID NO 1
<211> LENGTH: 12
<212> TYPE: DNA
<213> ORGANISM: Artificial Sequence
<220> FEATURE:
<223> OTHER INFORMATION: DNA-Oligonukleotidfragment, Fig. 1, 7b

<400> SEQUENCE: 1
taacattcag ag                                                         12

<210> SEQ ID NO 2
<211> LENGTH: 12
<212> TYPE: DNA
<213> ORGANISM: Artificial Sequence
<220> FEATURE:
<223> OTHER INFORMATION: DNA-Oligonukleotidfragment, Fig. 1, 7c

<400> SEQUENCE: 2
ggaggaccag ta                                                         12

<210> SEQ ID NO 3
<211> LENGTH: 12
<212> TYPE: DNA
<213> ORGANISM: Artificial Sequence
<220> FEATURE:
<223> OTHER INFORMATION: DNA-Oligonukleotidfragment, Fig. 1, 7d

<400> SEQUENCE: 3
accagattac aa                                                         12
```

The particles 10 with the oligonucleotides 7b, 7c, 7d, 7e remain in the cavities 15, so that each particle may again serve as a primary array for a renewed copying operation with a new support. It is thus possible to produce virtually any number of copies.

To again prepare the primary array (the sequencer chip 14) for an additional copy cycle after the copying operation, the amplification agent in the cavities, for example, the PCR mix, can be replaced or removed.

Figure 5:
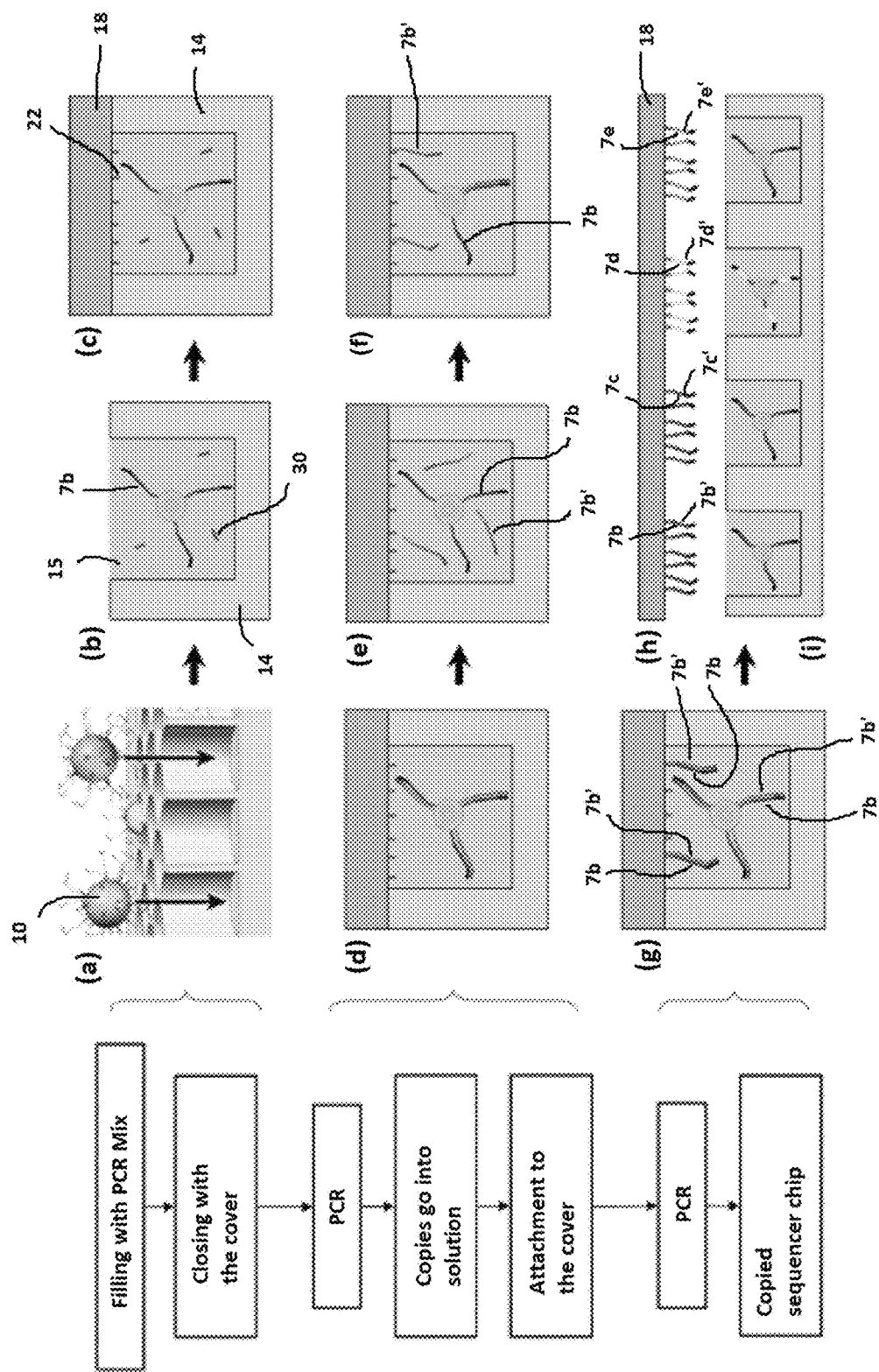
FIG. 5 shows an exemplary embodiment with the beads 10 each carrying different oligonucleotides but with the same terminal sequences. The process is illustrated on the basis of the oligonucleotide 7b.

Exemplary Embodiment b) (FIG. 5)

The beads 10 each carry different oligonucleotides but with the same terminal sequences. This process is illustrated

The invention claimed is:

1. A method for identifying aptamers, comprising
bringing a mixture of oligonucleotides in contact with an aptamer-target structure and binding at least some of the oligonucleotides to the target structure,
separating all oligonucleotides that have bound to the aptamer-target structure from the aptamer-target structure and from oligonucleotides not bound to the aptamer-target structure,
spatially separate amplification of individual oligonucleotides of all of said oligonucleotides that have bound to the aptamer-target structure, wherein each of the individual oligonucleotides is amplified spatially separate from one another resulting in several spatially separate amplicons, wherein each amplicon primarily contains one type of oligonucleotide, issuing a specific marker to a plurality of the spatially separate amplicons, so that each of the amplicons that have been marked is unambiguously identifiable on the basis of its specific marker, sequencing oligonucleotides in a plurality of the amplicons that have been marked, and assigning the specific marker for that amplicon to the sequence of a type of oligonucleotides in the amplicon to provide types of oligonucleotides, analysis of the binding properties of all of said types of oligonucleotides to the aptamer-target structure and assigning the analyzed binding properties to the specific markers of the amplicons and the sequences of the types of oligonucleotides.

2. The method according to claim 1, wherein the spatially separate amplification is an amplification in an emulsion, a digital amplification or an amplification on a solid phase.

3. The method according to claim 1, wherein the specific marker is a location position or an optically, spectroscopically or radioactively detectable marker.

4. The method according to claim 1, comprising the arrangement of the amplicons in locally separate regions in or on one or more first support(s), wherein an array of the amplicons is obtained, in which a specific location marker is issued to each amplicon as a specific marker.

5. The method according to claim 4, comprising binding of the oligonucleotides before, during or after the spatially separate amplification on solid-phase particles, yielding solid-phase particles to which only one amplicon with one type of oligonucleotide is bound.

6. The method according to claim 5, comprising
bringing the solid-phase particles to which an amplicon with one type of oligonucleotide is bound in contact with the aptamer-target structure,
detecting a positive or negative binding event of the aptamer-target structure to the oligonucleotides of the amplicon which is bound to a solid-phase particle,
selection of solid-phase particles in which a positive binding event can be detected.

7. The method according to claim 1, wherein for analysis of the binding properties an array of the amplicons is brought in contact with the aptamer-target structure.

8. The method according to claim 4, comprising
creating a copy or a derivative of the array of the amplicons in or on a second support, wherein a specific location marker is assigned to each amplicon of the copy or of the derivative as a specific marker,
bringing the copy or the derivative of the array in contact with the aptamer-target structure for analysis of the binding properties.

9. The method according to claim 8, wherein the second support has a binding adapter for oligonucleotides of the amplicons or binding properties for oligonucleotides of the amplicons, and the copy is created by binding nucleotides from the amplicons to the support by means of the binding adapter or the binding properties.

10. The method according to claim 9, comprising
providing at least one spatially limited amplification agent region for each oligonucleotide that is separated from the amplification agent regions of the other oligonucleotides, wherein a surface of the second support, which is provided with the binding adapter or binding properties, is adjacent to the amplification agent regions,
amplifying the oligonucleotides by means of amplification agents in the amplification agent regions for creating amplicons of the oligonucleotides,
binding single strands or derivatives of the amplicons to the second support by means of the binding adapter or the binding properties, so that a spatial arrangement of the single strands on the second support corresponds to the spatial arrangement of the amplicons in the array from which the single strands originate, and
removing the second support with the bound single strands from the array.

11. The method according to claim 10, wherein the binding of the copies or derivatives to the second support takes place simultaneously with the amplification.

12. The method according to claim 10, wherein the spatially limited amplification agent regions are defined at least partially by micro-or nanostructures in the first support, which carries the array, or in the second support, which carries the copy or the derivative.

13. The method according to claim 12, wherein creating at least one spatially limited amplification agent region for each oligonucleotide comprises providing the oligonucleotides in respectively assigned separate recesses in the first support, introducing the amplification agent into the recesses and closing the recesses by using the second support.

14. The method according to claim 12, wherein creating at least one spatially limited amplification agent region comprises providing the second support with at least one recess assigned to each oligonucleotide, in which the binding adapter is arranged, introducing the amplification agent into the recesses and closing the recesses by means of the first support, so that the oligonucleotides are exposed to the amplification agent region.

15. The method according to claim 10, wherein the spatially limited amplification agent regions are separated at least partially by phase boundaries between two liquids, a liquid and a gas or a physical barrier.

16. The method according to claim 4, comprising the recovery of one or more types of oligonucleotides by releasing the oligonucleotides from the first support, the second support and/or copies of these supports.

17. The method according to claim 4, comprising the production of additional oligonucleotides by amplification of oligonucleotides bound to the first support, the second support and/or copies of these supports.

18. The method for identifying aptamer binding pairs, which bind to various locations on an aptamer-target structure according to claim 4, further comprising:
a) bringing the array of the amplicons or the copy of the array of the amplicons in contact with the aptamer-target structure and binding the aptamer-target structure to oligonucleotides contained in amplicons of the array/the copy of the array,
b) bringing the array or the copy of the array obtained in a) in contact with a mixture of oligonucleotides and binding at least some of the oligonucleotides to the aptamer-target structure, which is already bound to the array,
c) elution of oligonucleotides that are not bound to the aptamer-target structure in b),
d) removing the oligonucleotides bound in b) from the aptamer-target structure,
e) sequencing the oligonucleotides obtained in d) and producing or isolating the oligonucleotides of one type, f) bringing an array of the amplicons or the copy of the array of the amplicons in contact with the aptamer-target structure and binding the aptamer-target structure to oligonucleotides present in amplification of the array/copy of the array, g) bringing the array of the copy of the array obtained in f) in contact with a oligonucleotide of one type from step e) and the binding of the oligonucleotide to one or more aptamer-target structures that are already bound to the array, h) analyzing which aptamer-target structure(s) on the array the oligonucleotide of one type has bound to and assigning the target structure to the oligonucleotide of the array to which it has bound and its specific location marker in the array, i) optionally repeating steps g) and h) one or more times.

19. The method according to claim 1, wherein the oligonucleotides comprise flanking sequences and wherein said flanking sequences are compatible with a primer sequences used for the sequencing processes.

* * * * *